United States Patent
Sakai et al.

(10) Patent No.: US 7,956,999 B2
(45) Date of Patent: Jun. 7, 2011

(54) RESISTIVITY TESTING METHOD AND DEVICE THEREFOR

(75) Inventors: Satoshi Sakai, Kanagawa (JP); Akemi Takano, Nagasaki (JP); Yasuyuki Kobayashi, Kanagawa (JP); Kengo Yamaguchi, Nagasaki (JP)

(73) Assignee: Mitsubishi Heavy Industries, Ltd. (JP)

( * ) Notice: Subject to any disclaimer, the term of this patent is extended or adjusted under 35 U.S.C. 154(b) by 0 days.

(21) Appl. No.: 12/934,717

(22) PCT Filed: Jul. 2, 2009

(86) PCT No.: PCT/JP2009/062117
§ 371 (c)(1),
(2), (4) Date: Sep. 27, 2010

(87) PCT Pub. No.: WO2010/018717
PCT Pub. Date: Feb. 18, 2010

(65) Prior Publication Data
US 2011/0019190 A1    Jan. 27, 2011

(30) Foreign Application Priority Data
Aug. 11, 2008 (JP) ................................. 2008-207062

(51) Int. Cl.
*G01J 4/00* (2006.01)
*G01B 11/28* (2006.01)

(52) U.S. Cl. ................. 356/369; 356/364; 356/630
(58) Field of Classification Search .......... 356/364–369, 356/445, 630
See application file for complete search history.

(56) References Cited

U.S. PATENT DOCUMENTS

| | | | |
|---|---|---|---|
| 7,167,241 B1 * | 1/2007 | Johs et al. | 356/364 |
| 7,782,471 B2 * | 8/2010 | Maris | 356/630 |
| 2005/0200850 A1 * | 9/2005 | Borden et al. | 356/432 |

FOREIGN PATENT DOCUMENTS

| | | |
|---|---|---|
| JP | 1-224646 A | 9/1989 |
| JP | 2001-59816 A | 3/2001 |
| JP | 2002-517750 A | 6/2002 |
| JP | 2002-517915 A | 6/2002 |
| JP | 2003-506675 A | 2/2003 |
| JP | 2004-221145 A | 8/2004 |
| JP | 2005-134324 A | 5/2005 |
| JP | 2007-225418 A | 9/2007 |

OTHER PUBLICATIONS

International Search Report of Application No. PCT/JP2009/062117 mailed Aug. 11, 2009.

* cited by examiner

*Primary Examiner* — L. G Lauchman
(74) *Attorney, Agent, or Firm* — Kanesaka Berner and Partners LLP

(57) ABSTRACT

An object is to efficiently measure the resistivity of a transparent conductive film with high accuracy in a non-destructive and non-contact manner. Provided is a resistivity testing device that includes a light emitting device that emits p-polarized emission light having a wavelength selected by a preliminarily performed test-condition selecting method toward a transparent conductive film, formed on a light-transmissive substrate conveyed along a manufacturing line, from a film-surface side at an incidence angle selected by the method; a light detecting device that detects reflected light reflected at the transparent conductive film; and an information processor that calculates an evaluation value related to the amount of light of the reflected light with respect to the wavelength on the basis of the intensity of the detected light and obtains a resistivity from the calculated evaluation value by using a correlation characteristic in which the evaluation value and the resistivity are associated with each other in advance.

12 Claims, 14 Drawing Sheets

CONVEYING DIRECTION (Y)

POLARIZATION IN X DIRECTION: P-POLARIZED LIGHT
POLARIZATION IN Y DIRECTION: S-POLARIZED LIGHT
Z DIRECTION: TRAVELING DIRECTION OF LIGHT

RESISTIVITY TESTING METHOD AND DEVICE THEREFOR

RELATED APPLICATIONS

The present application is based on International Application Number PCT/JP2009/062117, filed Jul. 2, 2009, and claims priority from Japanese Application Number 2008-207062, filed Aug. 11, 2008, the disclosures of which are hereby incorporated by reference herein in their entirety.

TECHNICAL FIELD

The present invention relates to a test-condition selecting method for selecting an incidence angle and a wavelength of emission light used for testing the resistivity of a transparent conductive film formed on a light-transmissive substrate, a resistivity testing method and a device therefor for testing the resistivity of a transparent conductive film by using the wavelength and incidence angle selected by this test-condition selecting method, a photoelectric-converter manufacturing apparatus for manufacturing a photoelectric converter that includes a transparent conductive film, and a photoelectric converter manufactured by the manufacturing apparatus.

BACKGROUND ART

In the related art, a method of measuring the resistance of a transparent conductive film formed on a light-transmissive substrate by utilizing optical transmission/reflection characteristics of the material is known (for example, see Patent Literature 1).

Patent Literature 1 discloses a technology in which, for example, a solar-cell substrate provided with a transparent conductive film is irradiated with light in a solar-cell manufacturing line, so as to evaluate the characteristics of the transparent conductive film on the basis of the reflectivity calculated from the light intensity of the irradiated light and the light intensity of reflected light.

CITATION LIST

Patent Literature

{PTL 1} Japanese Unexamined Patent Application, Publication No. 2007-225418

SUMMARY OF INVENTION

Technical Problem

Patent Literature 1 mentioned above discloses that, when evaluating the sheet resistance of a transparent conductive film, emission light in a wavelength range between 2400 nm and 3000 nm is used, whereas when evaluating the resistivity of a transparent conductive film, emission light in a wavelength range between 1500 nm and 1800 nm is used.

The reason that the wavelength of emission light is varied between when evaluating the resistivity and when evaluating the sheet resistance is because resistivity cannot be measured using the emission light in the wavelength range between 2400 nm and 3000 nm due to a low correlation between resistivity and reflectivity, and likewise, sheet resistance cannot be measured using the emission light in the wavelength range between 1500 nm and 1800 nm due to a low correlation between sheet resistance and reflectivity (for example, see paragraphs [0048] to [0052] in Patent Literature 1).

The method disclosed in Patent Literature 1 mentioned above has a problem in that it provides a low degree of freedom for wavelength selection since the wavelength range that can be used for measuring the resistivity is limited to a narrow range of 1500 nm to 1800 nm.

The present invention has been made in view of the aforementioned problem, and an object thereof is to provide a resistivity testing method and a device therefor that allow for selection of an appropriate wavelength to be used for measuring the resistivity from a wider wavelength range and also allow for efficient measurement of the resistivity of a transparent conductive film with high accuracy in a non-destructive and non-contact manner, a test-condition selecting method for selecting a test condition to be used in the resistivity testing method and the device therefor, a photoelectric-converter manufacturing apparatus that includes the resistivity testing device, and a photoelectric converter manufactured by the manufacturing apparatus.

Solution to Problem

To solve the aforementioned problem, the present invention provides the following solutions.

A first aspect of the present invention provides a test-condition selecting method for selecting a wavelength and an incidence angle of emission light used for testing the resistivity of a transparent conductive film, the method including emitting p-polarized emission light rays having different test conditions, including wavelengths and incidence angles, to a plurality of transparent conductive films having different combinations of film thicknesses and resistivities so as to measure evaluation values related to amounts of light of reflected light rays thereof; obtaining a correlation in which the test conditions, the evaluation values, and sample conditions are associated with each other, the sample conditions including combinations of the film thicknesses and the resistivities of the transparent conductive films; and selecting one of the test conditions in the correlation, the test condition being such that an error in the corresponding evaluation value due to the different film thicknesses of the transparent conductive films is within a tolerable range and a change in the evaluation value relative to a change in the corresponding resistivity is greater than or equal to a predetermined value.

Based on the following experiments and examinations, the present inventors have discovered that, when measuring the resistivity of a transparent conductive film, it is necessary to eliminate a measurement error occurring due to the film thickness.

First, the present inventors prepared transparent conductive films having the same resistivity but different film thicknesses as test samples. In this case, four film thicknesses were used, namely, 75 nm, 150 nm, 300 nm, and 600 nm, respectively. Then, the prepared transparent conductive films were each irradiated with light with wavelengths ranging from 300 nm to 5000 nm, and the reflectivity for each wavelength was obtained from reflected light obtained at that time. Moreover, from this wavelength, the wavelengths 1500 nm and 2400 nm disclosed in Patent Literature 1 were selected, and a sheet-resistance-versus-reflectivity relationship corresponding to each of these wavelengths was obtained.

FIG. 18 shows a wavelength-reflectivity correlation diagram for the respective film thicknesses, FIG. 19 illustrates the sheet-resistance-versus-reflectivity relationship for each film thickness when a wavelength of 1500 nm is used, and FIG. 20 illustrates the sheet-resistance-versus-reflectivity relationship for each film thickness when a wavelength of 2400 nm is used. In FIGS. 18 to 20, numerical values 75 nm, 150 nm, 300 nm, 600 nm written in each graph denote the film thicknesses of transparent conductive films.

As shown in FIGS. 18 and 19, it is apparent that the reflectivity when the wavelength of 1500 nm is used has low film-thickness dependency and that the sheet resistance cannot be measured.

In contrast, as shown in FIGS. 18 and 20, it is apparent that the reflectivity when the wavelength of 2400 nm is used has high film-thickness dependency. In other words, at the wavelength of 2400 nm, a change in the film thickness is exhibited instead of a change in the resistivity, making it apparent that there is a change in the sheet resistance. Specifically, at the wavelength of 2400 nm, the film thickness cannot be disregarded as an error factor, and it was discovered that, when measuring the resistivity using this wavelength range, a crucial factor for increasing the resistivity measurement accuracy is how this error factor owing to the film thickness can be eliminated.

In light of this, the present inventors have proposed utilizing the Brewster effect for eliminating the effect of the film thickness, which is an error factor. Specifically, in the proposal, measurement errors owing to the film thickness can be eliminated by using an optical system that utilizes the Brewster effect to cut reflected light including interference components caused by a multiple interference effect inside the transparent conductive film and that optically receives only reflected components in a long wavelength range resulting from free-electron absorption with which resistivity is involved.

FIG. 21 is a diagram illustrating an optical calculation model of the Brewster effect. In the Brewster effect, p-polarized emission light is first emitted to the transparent conductive film. In FIG. 21, a refractive index n1 corresponds to the atmosphere and a refractive index n2 corresponds to the transparent conductive film, and the emission light is reflected at the boundary between the atmosphere and the transparent conductive film.

In this Brewster effect, it is expected that the resistivity can be measured with high accuracy without being affected by the film thickness by setting the wavelength and the incidence angle of the emission light to appropriate values. Therefore, as described above, in the present invention, the reflectivity-versus-wavelength relationships when the test conditions of the emission light including wavelengths and incidence angles are changed respectively are obtained, and an appropriate wavelength and an appropriate incidence angle are selected from these relationships. Thus, in the actual resistivity testing process, a measurement error can be reduced, thereby increasing the accuracy in testing.

When testing the resistivity of the transparent conductive film, because the surface condition (roughness condition) of the transparent conductive film and the temperature can also possibly be factors for a measurement error other than the aforementioned film thickness, the present inventors have also examined these factors.

First, the surface condition of the transparent conductive film is generally quantified as a haze ratio.

When using the test-condition selecting method of the present invention, although an appropriate wavelength is selected from a wavelength range substantially between 1500 nm and 4000 nm, it was apparent, as shown in FIG. 22, that the haze ratio has hardly any effect in this wavelength range. Therefore, when using a wavelength of substantially 1400 nm or greater, the haze ratio, in other words, a measurement error resulting from the surface condition of the transparent conductive film, can be eliminated.

FIG. 23 is a graph illustrating wavelength dependency of blackbody radiation. The ordinate represents the thermal radiation intensity (erg), whereas the abscissa represents the wavelength (nm). A conceivable temperature range when performing the measurement on the transparent conductive film is from room temperature to 100° C., and it is apparent that light with a wavelength up to about 4000 nm is hardly emitted. Therefore, with regard to a wavelength of 4000 nm or smaller, when performing the measurement on the transparent conductive film, there is no effect of the temperature or such an effect can be eliminated in the conceivable temperature range.

Accordingly, with the test-condition selecting method of the present invention, a test condition that allows for elimination of a measurement error due to not only the film thickness but also the haze ratio or the temperature can be selected.

A second aspect of the present invention provides a resistivity testing method that includes emitting p-polarized emission light having a wavelength selected by the aforementioned test-condition selecting method toward a transparent conductive film, formed on a light-transmissive substrate conveyed along a manufacturing line, from a film-surface side at an incidence angle selected by the test-condition selecting method; detecting reflected light reflected at the transparent conductive film; calculating an evaluation value related to the amount of light of the reflected light with respect to the wavelength selected by the test-condition selecting method on the basis of the intensity of the detected reflected light; and obtaining a resistivity from the calculated evaluation value by using a correlation characteristic in which the evaluation value and the resistivity are associated with each other in advance.

With the aforementioned resistivity testing method, the resistivity of the transparent conductive film formed on the light-transmissive substrate conveyed along a manufacturing line can be efficiently measured in a non-destructive and non-contact manner.

Moreover, since an appropriate condition selected by the aforementioned test-condition selecting method is used as the test condition, the resistivity can be measured without being affected by the film thickness, the haze ratio, the temperature, or the like.

A third aspect of the present invention provides a resistivity testing device that includes a light emitter that emits p-polarized emission light having a wavelength selected by the aforementioned test-condition selecting method toward a transparent conductive film, formed on a light-transmissive substrate conveyed along a manufacturing line, from a film-surface side at an incidence angle selected by the test-condition selecting method; a light detector that detects reflected light reflected at the transparent conductive film; an evaluation-value calculator that calculates an evaluation value related to the amount of light of the reflected light with respect to the wavelength selected by the test-condition selecting method on the basis of the intensity of the detected reflected light; and a resistance-value calculator that obtains a resistivity from the calculated evaluation value by using a correlation characteristic in which the evaluation value and the resistivity are associated with each other in advance.

With the aforementioned resistivity testing device, the resistivity of the transparent conductive film formed on the light-transmissive substrate conveyed along a manufacturing line can be efficiently measured in a non-destructive and non-contact manner.

Moreover, since an appropriate condition selected by the aforementioned test-condition selecting method is used as the test condition, the resistivity can be measured without being affected by the film thickness or the like.

In the aforementioned resistivity testing device, the light emitter may include a light source that emits the emission light having the wavelength, and a polarizer that converts the emission light emitted from the light source to the p-polarized emission light. In this case, for example, a light-emitting diode may be used as the light source.

In the aforementioned resistivity testing device, the light emitter may include a light source that emits the emission light in a predetermined wavelength range that includes the wavelength; a polarizer that converts the emission light emitted from the light source to the p-polarized emission light; and a wavelength selector provided in an optical path of the emission light emitted from the light source or in an optical path of the reflected light reflected at the transparent conductive film and configured to transmit light having the wavelength selected by the test-condition selecting method and to block other wavelengths.

In the aforementioned resistivity testing device, the light emitter may include a semiconductor laser that emits the emission light having the wavelength as a light source.

The aforementioned resistivity testing device may further include a light splitter provided in an optical path of emission light emitted from the light source and configured to split off a portion of the emission light; and a split-light detector that detects the light split off by the light splitter, and the evaluation-value calculator may calculate the evaluation value by using a detection result of the split-light detector.

By detecting a portion of the emission light in this manner, the light intensity of the emission light emitted to the transparent conductive film can be ascertained, thereby further increasing the reflectivity measurement accuracy. Thus, the resistivity measurement accuracy can be increased.

In the aforementioned resistivity testing device, at least one of the light emitter and the light detector may be surrounded by a light shielding member.

By surrounding the light emitter with the light shielding member in this manner, entry of ambient light can be suppressed. As a result, the resistivity measurement accuracy can be increased.

A fourth aspect of the present invention provides a photoelectric-converter manufacturing apparatus that includes the aforementioned resistivity testing device provided in a conveyor line.

It is preferable that the aforementioned photoelectric-converter manufacturing apparatus further include a cooling device that cools a light-transmissive substrate on which the transparent conductive film is formed, and the resistivity testing device is provided on a downstream side of the cooling device.

With such a configuration, the transparent conductive film with a stable temperature cooled by the cooling device can be the target object to be measured. Consequently, a measurement error due to the effect of the temperature can be eliminated.

A fifth aspect of the present invention provides a photoelectric converter manufactured by any one of the aforementioned photoelectric-converter manufacturing apparatus.

Advantageous Effects of Invention

The present invention advantageously achieves an ability to select an appropriate wavelength to be used for measuring the resistivity from a wider wavelength range, as well as an ability to efficiently measure the resistivity of a transparent conductive film with high accuracy in a non-destructive and non-contact manner.

DESCRIPTION OF EMBODIMENTS

A resistivity testing method and a device therefor, a test-condition selecting method for selecting a test condition to be used in the resistivity testing method and the device therefor, a photoelectric-converter manufacturing apparatus that includes the resistivity testing device, and a photoelectric converter manufactured by the manufacturing apparatus according to embodiments of the present invention will be described below with reference to the drawings.

Although the following description is directed to an example where a target test object is a transparent conductive film used in a photoelectric converter, such as a solar cell panel, the present invention is not limited to this, and the target test object may alternatively be a transparent conductive film used in a display, a windowpane, or the like.

A test-condition selecting method according to an embodiment of the present invention will be described below with reference to FIG. 1.

The test-condition selecting method according to this embodiment is for selecting a wavelength and an incidence angle of emission light used for measuring the resistivity of a transparent conductive film formed on a light-transmissive substrate, such as a glass substrate.

Figure 1:
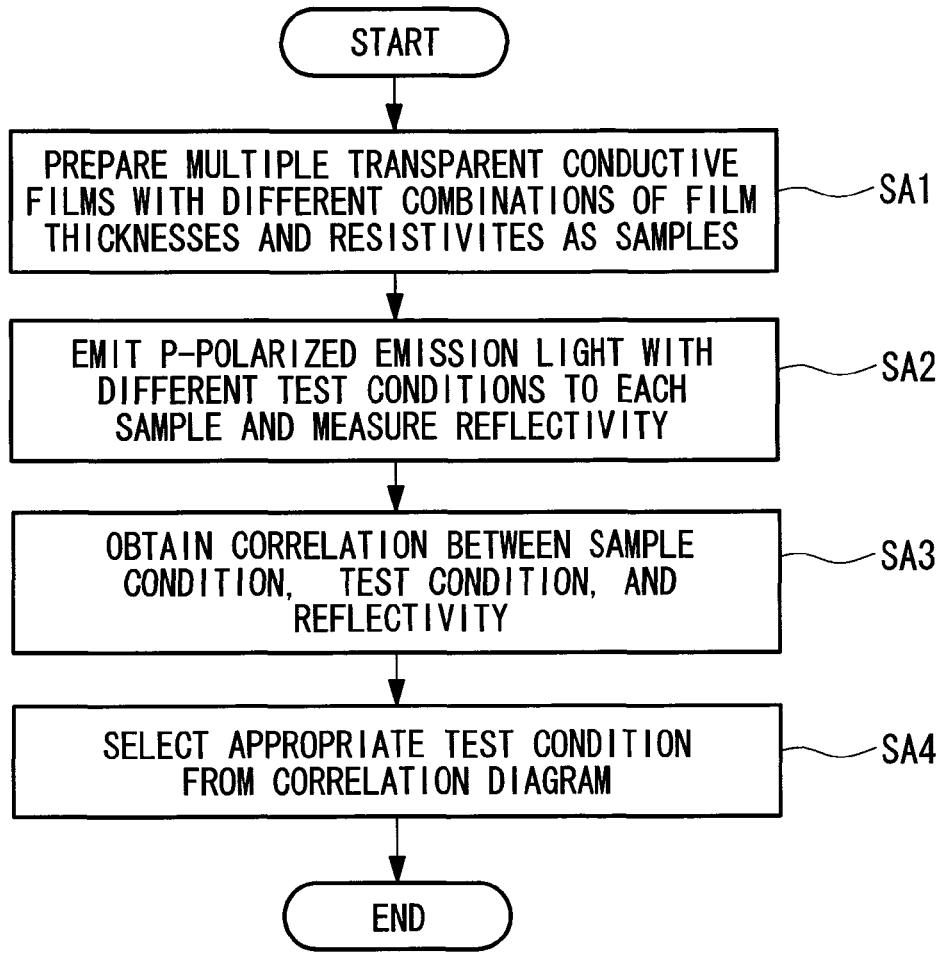
FIG. 1 is a flow chart that explains the procedure of a test-condition selecting method according to an embodiment of the present invention.

First, multiple transparent conductive films with different combinations of film thicknesses and resistivities are prepared as samples (step SA1 in FIG. 1). In this embodiment, eight samples with combinations shown in the following table are prepared.

TABLE 1

| SAMPLE NO. | RESISTIVITY ($10^{-4}$ Ωcm) | FILM THICKNESS (nm) |
|---|---|---|
| 1 | 5.9 | 600 |
| 2 | 6.3 | 600 |
| 3 | 6.6 | 600 |
| 4 | 7.1 | 600 |
| 5 | 5.9 | 800 |
| 6 | 6.3 | 800 |
| 7 | 6.6 | 800 |
| 8 | 7.1 | 800 |

Figure 2:
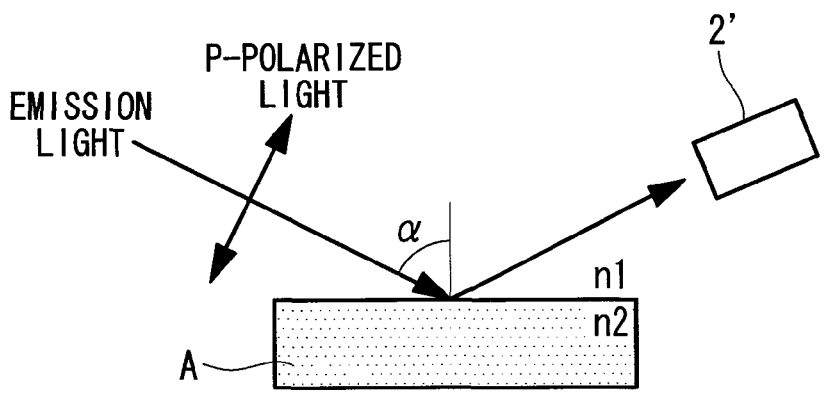
FIG. 2 is a diagram illustrating an example of an optical system model used when emitting emission light to a sample and optically receiving reflected light obtained at that time.
Figure 3:
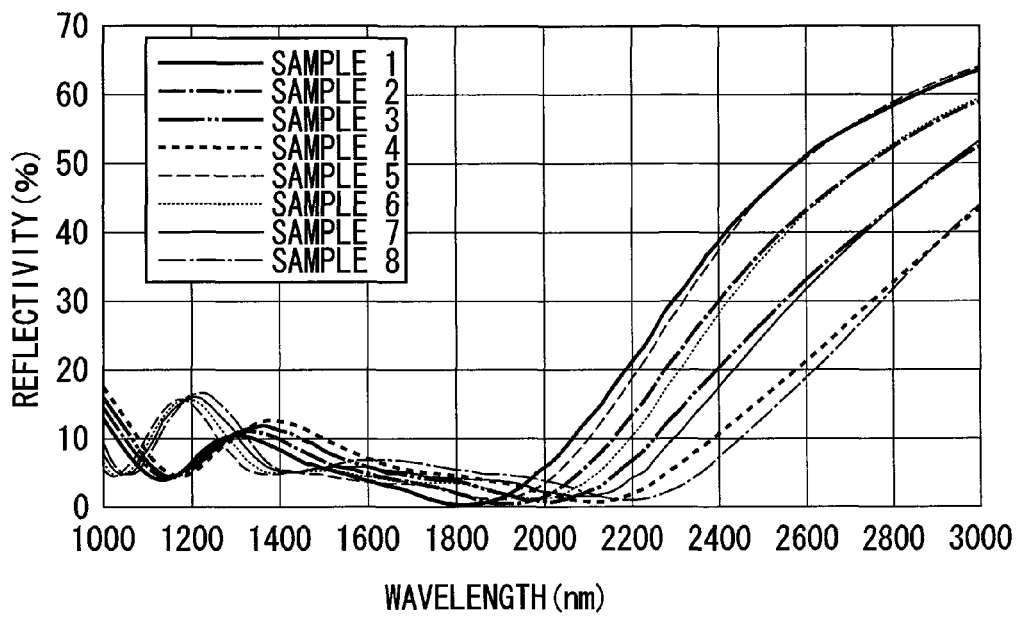
FIG. 3 shows reflectivity-versus-wavelength characteristics illustrating the relationship between the reflectivity and each wavelength ranging between 1000 nm and 3000 nm when the incidence angle is 0°.
Figure 4:
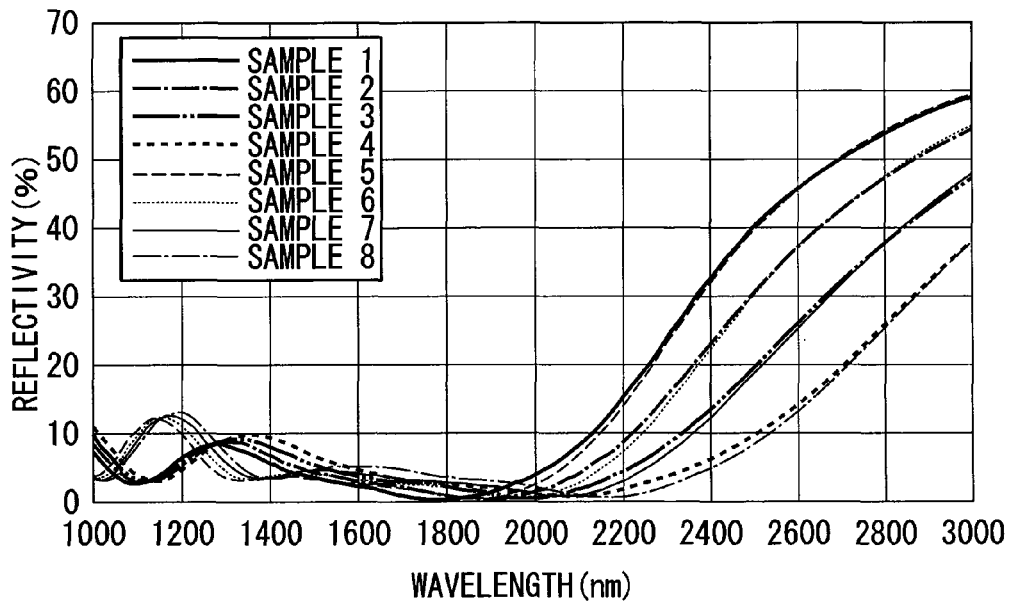
FIG. 4 shows reflectivity-versus-wavelength characteristics illustrating the relationship between the reflectivity and each wavelength ranging between 1000 nm and 3000 nm when the incidence angle is 30°.
Figure 5:
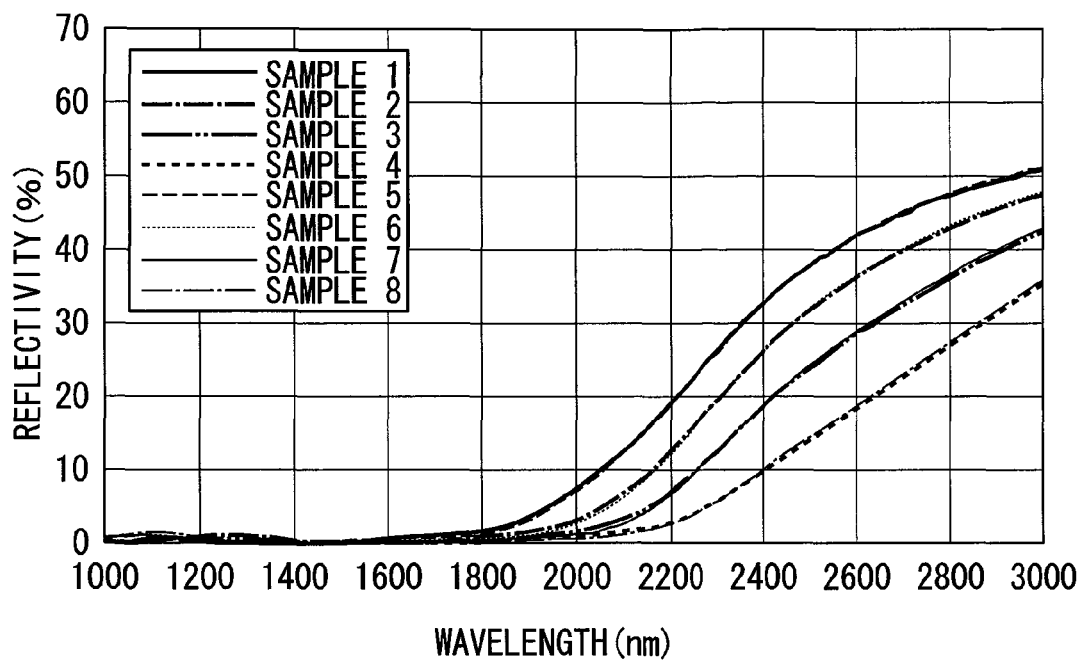
FIG. 5 shows reflectivity-versus-wavelength characteristics illustrating the relationship between the reflectivity and each wavelength ranging between 1000 nm and 3000 nm when the incidence angle is 60°.
Figure 6:
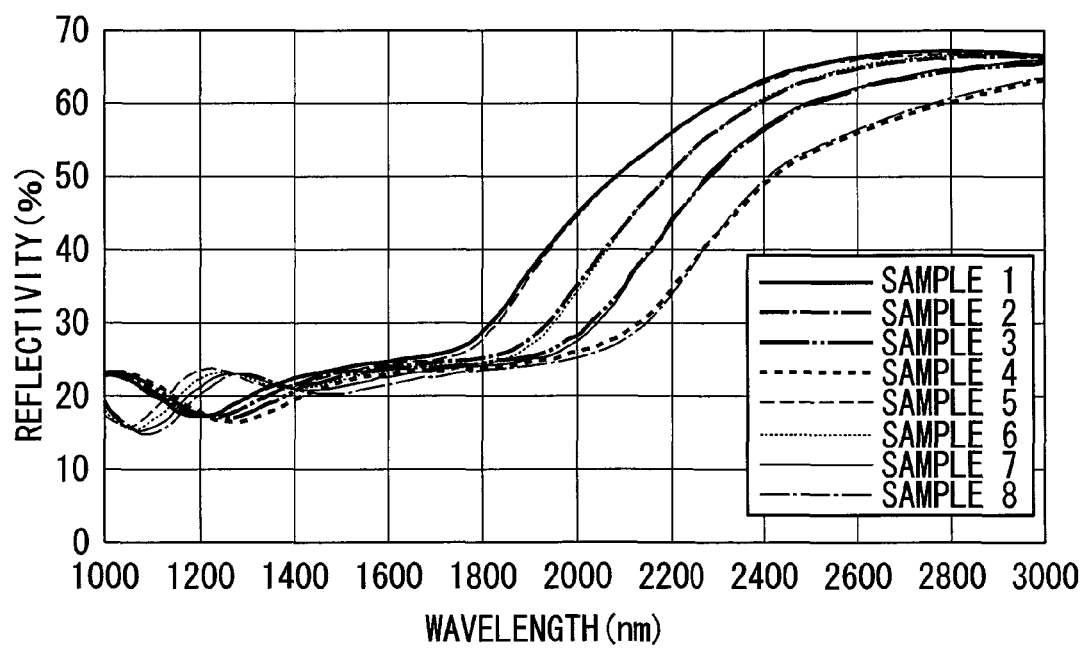
FIG. 6 shows reflectivity-versus-wavelength characteristics illustrating the relationship between the reflectivity and each wavelength ranging between 1000 nm and 3000 nm when the incidence angle is 80°.

Subsequently, as shown in FIG. 2, each of the transparent-conductive-film samples A from Nos. 1 to 8 above is irradiated with p-polarized emission light while changing the test conditions thereof, including wavelength and incidence angle, and reflected light obtained at that time is received by a light detector 2'; based on the light reception result, an evaluation value related to the amount of light (i.e., reflectivity in this embodiment) is measured (step SA2 in FIG. 1). In this case, an incidence angle α is defined as an angle of a film surface of each transparent-conductive-film sample A relative to the normal to the film surface. In this embodiment, the wavelength of emission light is varied within a range between 1000 nm and 4000 nm, and the incidence angle α is varied within a range between 0° and 90°.

When the measurement of the reflectivity for each test condition is completed, correlation diagrams each of which associates a sample condition including a combination of a film thickness and a resistivity of a transparent conductive film, a test condition including a wavelength and an incidence angle, and a reflectivity with each other are subsequently obtained (step SA3 in FIG. 1).

FIGS. 3, 4, 5, and 6 show reflectivity-versus-wavelength characteristics illustrating the relationship between the reflectivity and each wavelength ranging between 1000 nm and 3000 nm when the incidence angle is 0° (i.e., normal incidence condition), when the incidence angle is 30°, when the incidence angle is 60°, and when the incidence angle is 80°, respectively.

In the correlation diagrams shown in FIGS. 3 to 6, a test condition in which an error in reflectivity due to different film thicknesses of transparent conductive films is within a tolerable range and in which a change in reflectivity relative to a change in resistivity is greater than or equal to a predetermined value is selected (step SA4). In other words, when samples with the same resistivity but with different film thicknesses are set as pairs, a test condition in which the reflectivity-versus-wavelength characteristics of the samples of the same pair substantially match and in which a resistivity-reflectivity correlation can be sufficiently confirmed is selected. In this embodiment, samples 1 and 5, samples 2 and 6, samples 3 and 7, and samples 4 and 8 form pairs. For example, in the condition shown in FIG. 5 where the incidence angle is 60°, it is apparent that the reflectivity-versus-wavelength characteristics of each pair have a higher matching rate, as compared with those in the other correlation diagrams. Furthermore, in FIG. 5, although there is no resistivity-reflectivity correlation in, for example, a wavelength range between 1000 nm and 1800 nm, there is a sufficient resistivity-reflectivity correlation in a wavelength range between 2200 nm and 3000 nm; in this wavelength range, it can be confirmed that the resistivity can be calculated with high accuracy from the reflectivity.

In this manner, in step SA4, a combination of incidence angle and wavelength with a sufficient resistivity-reflectivity correlation is selected in each of the correlation diagrams shown in FIGS. 3 to 6.

Regarding such selection of the test conditions, an operator may manually perform the selection by checking each correlation diagram, or the selection may be performed automatically on the basis of software processing or the like using a computer. In the case of automatic selection, it is conceivable to pre-register a condition that "an error in reflectivity due to different film thicknesses of transparent conductive films is within a tolerable range and a change in reflectivity relative to a change in resistivity is greater than or equal to a predetermined value", and to construct a program so as to select a wavelength corresponding to the highest resistivity-reflectivity correlation from test conditions that satisfy the aforementioned condition. As an alternative configuration, the test conditions that satisfy the aforementioned condition may be extracted by software processing and the operator may select a desired test condition from the extracted test conditions.

The tolerable range for an error in reflectivity due to different film thicknesses and the predetermined value for evaluating the relationship between the resistivity and the reflectivity can be set in a freely-chosen manner.

Accordingly, with the test-condition selecting method according to this embodiment, multiple samples are prepared and the reflectivity is obtained when each of these samples is irradiated with emission light under multiple test conditions, so that a test condition can be selected on the basis of a resistivity-reflectivity correlation, thereby allowing for selection of an optimal test condition. Thus, by employing the selected test condition in the actual testing, a measurement error due to the effect of the film thickness or the like can be eliminated, whereby the resistivity can be obtained with high accuracy.

Figure 7:
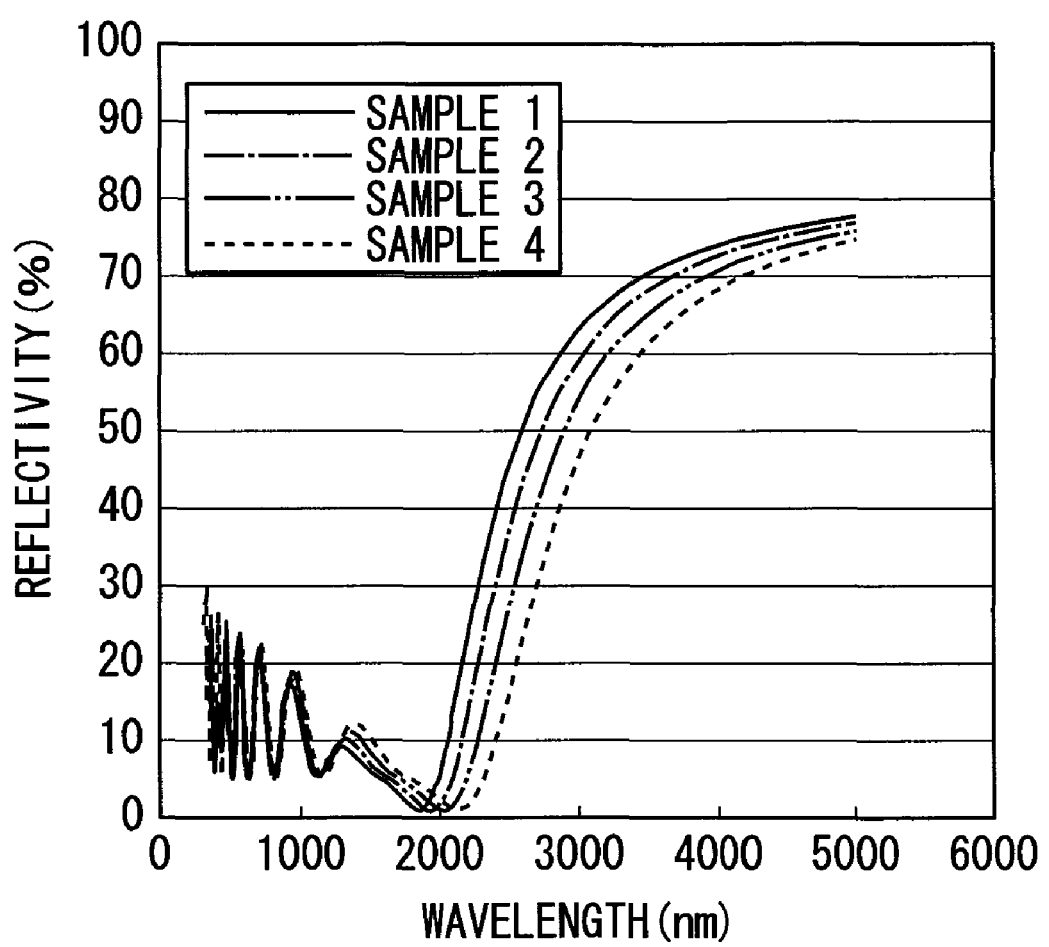
FIG. 7 is an example of a wavelength-reflectivity correlation diagram when testing is performed in a wavelength range between 300 nm and 5000 nm.

In the above-described embodiment, although the wavelength is varied in a range between 1000 nm and 3000 nm, the above-described test may be performed using a wider wavelength range. For example, FIG. 7 illustrates an example of a correlation diagram when the testing is performed in a wavelength range between 300 nm and 5000 nm. As shown in this diagram, it is apparent that there is a sufficient resistivity-reflectivity correlation when the wavelength is substantially equal to 4000 nm. Furthermore, it is apparent from the correlation diagram in FIG. 7 that there is a sufficient resistivity-reflectivity correlation in a wavelength range between 2000 nm and 4500 nm, and particularly, there is a strong resistivity-reflectivity correlation in a range between 2500 nm and 4000 nm. Therefore, in view of these results, in the above-described test-condition selecting method, it is sufficient so long as the wavelength is varied in the range between 2000 nm and 4500 nm, and more preferably, the wavelength may be varied in the range between 2500 nm and 4000 nm.

Based on the results in FIGS. 3 to 6, the incidence angle may be varied in a range between 30° and 75°, more preferably, in a range between 40° and 70°.

Next, each of embodiments of a resistivity testing method and a resistivity testing device for measuring and evaluating the resistivity of a transparent conductive film formed on a light-transmissive substrate by using an incidence angle and a wavelength selected by the above-described test-condition selecting method will be described with reference to the drawings.

First Embodiment

Figure 8:
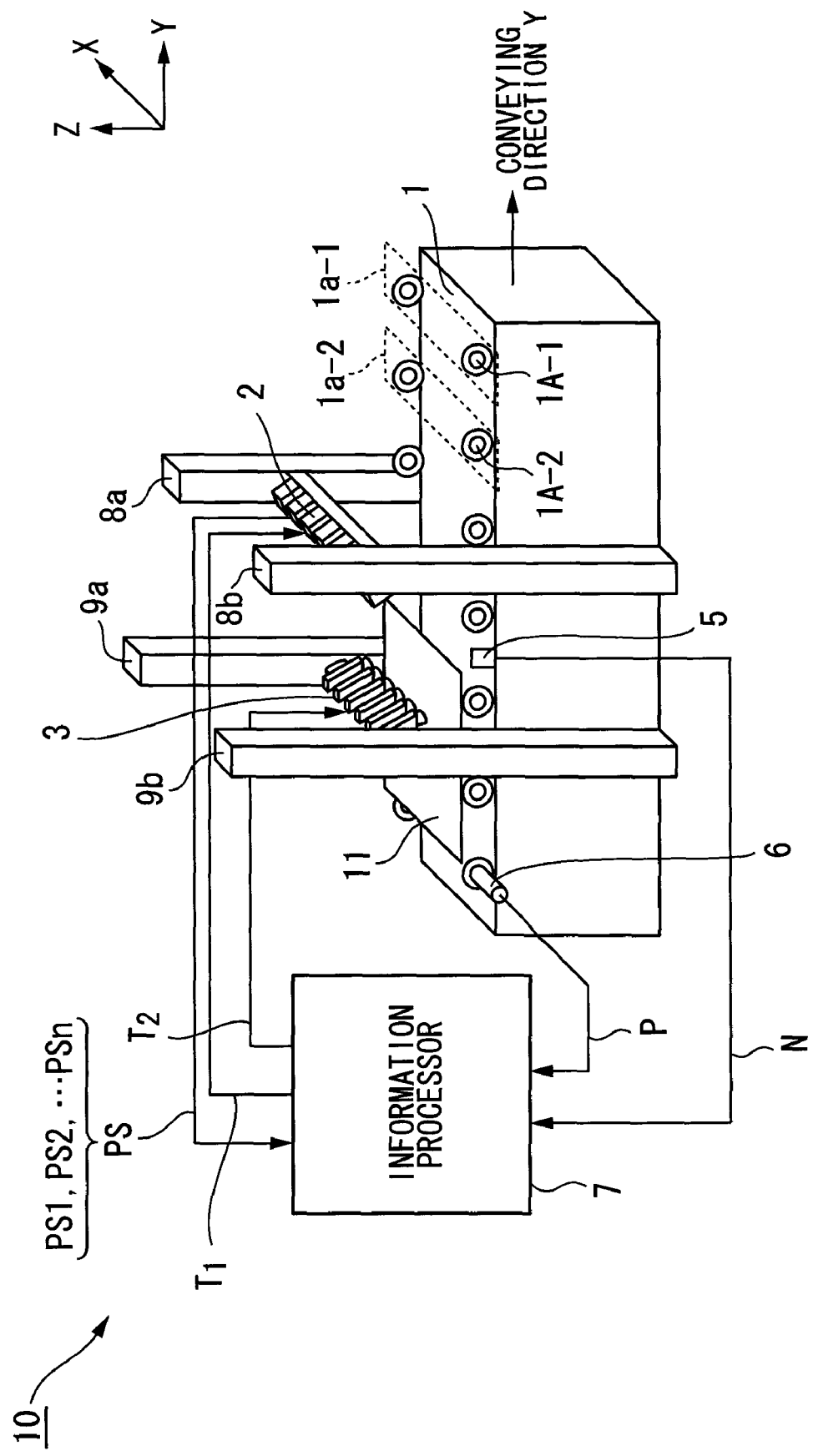
FIG. 8 is a diagram illustrating the schematic configuration of a resistivity testing device according to a first embodiment of the present invention.

FIG. 8 is a diagram illustrating the schematic configuration of a resistivity testing device according to a first embodiment of the present invention. A resistivity testing device 10 includes a conveyor 1, a light detecting device (light detector) 2, a light emitting device (light emitter) 3, a position sensor 5, a rotary encoder 6, an information processor (an evaluation-value calculator and a resistance-value calculator) 7, detector securing members 8 (8a and 8b), and light-source securing members 9 (9a and 9b).

The conveyor 1 includes a plurality of rollers 1a-1 to 1a-n each constituted of a roller pair for conveying a substrate 11 having a transparent conductive film formed thereon. Each roller 1a-i (i=1, 2, . . . , or n, and the same hereinafter) is in contact with the substrate 11. The plurality of the rollers 1a-1 to 1a-n are arranged in order in a conveying direction Y of the substrate 11 and are rotated simultaneously in a predetermined direction at a predetermined rotation speed so as to convey the substrate 11 in the conveying direction Y.

Figure 10:
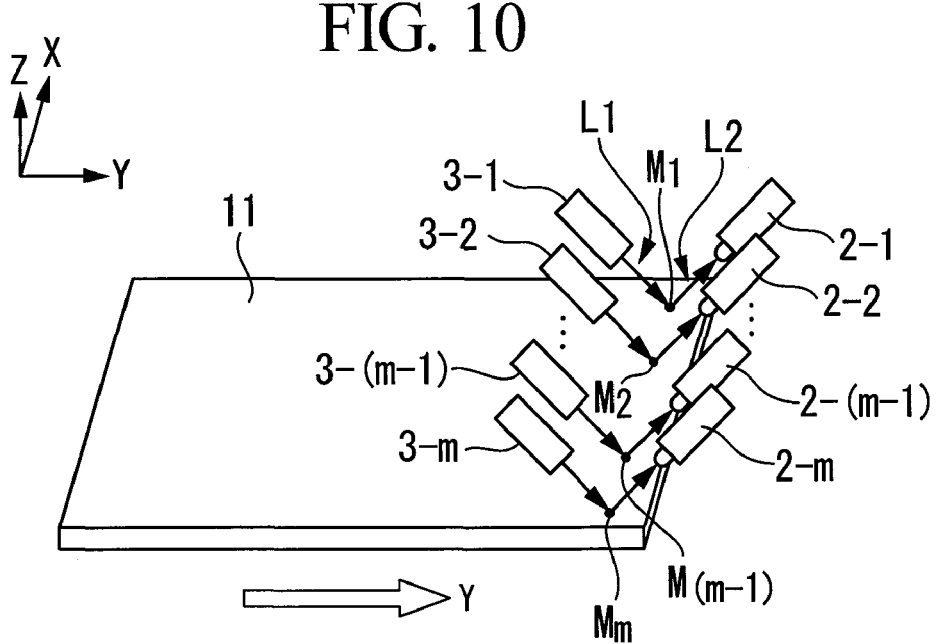
FIG. 10 is a schematic diagram illustrating the positional relationship between multiple light emitters and multiple light detectors.

The light detecting device 2 includes a plurality of light detectors 2-1 to 2-m (see FIG. 10). For example, the light detecting device 2 includes eight light detectors 2-1 to 2-8. The light detecting device 2 is securely disposed above (Z direction) a conveying surface of the conveyor 1 (i.e., a surface along which the substrate 11 is conveyed) by the detector securing members 8 (8a and 8b) fixed to opposite side surfaces of the conveyor 1 in an X direction thereof. On the basis of a trigger signal T1 output from the information processor 7, each light detector 2-j (j=1, 2, . . . , or m, and the same hereinafter) optically receives reflected light reflected from the transparent conductive film on the substrate 11. An intensity PS of the reflected light is then output to the information processor 7. The light detectors 2-j used here are capable of optically receiving light with a wavelength that corresponds to the wavelength of light emitted from light emitters 3-j, to be described below. Examples of the light detectors 2-j include photodetectors and CCD (charge-coupled device) sensors.

The light emitting device 3 includes a plurality of light emitters 3-1 to 3-m (see FIG. 10). For example, the light emitting device 3 includes eight light emitters 3-1 to 3-8. The light emitters 3-j and the light detectors 2-j form pairs. The light emitting device 3 is securely disposed above (Z direction) the conveying surface of the conveyor 1 (i.e., the surface along which the substrate 11 is conveyed) by the light-source securing members 9 (9a and 9b) fixed to the opposite side surfaces of the conveyor 1 in the X direction thereof. The light-source securing members 9 (9a and 9b) are disposed on the front side in the conveying direction Y relative to the detector securing members 8 (8a and 8b). It should be noted, however, that the positional relationship between the light-source securing members 9 (9a and 9b) and the detector securing members 8 (8a and 8b) can be inverted.

Alternatively, the light emitting device 3 may be a line light source. For example, a linear light source having LEDs arranged in a line can be used as the line light source. With such a light emitting device 3, since the point source and the directivity are reduced, an optical system (lens or collimator) for guiding the light to a measurement position is required.

Figure 9:
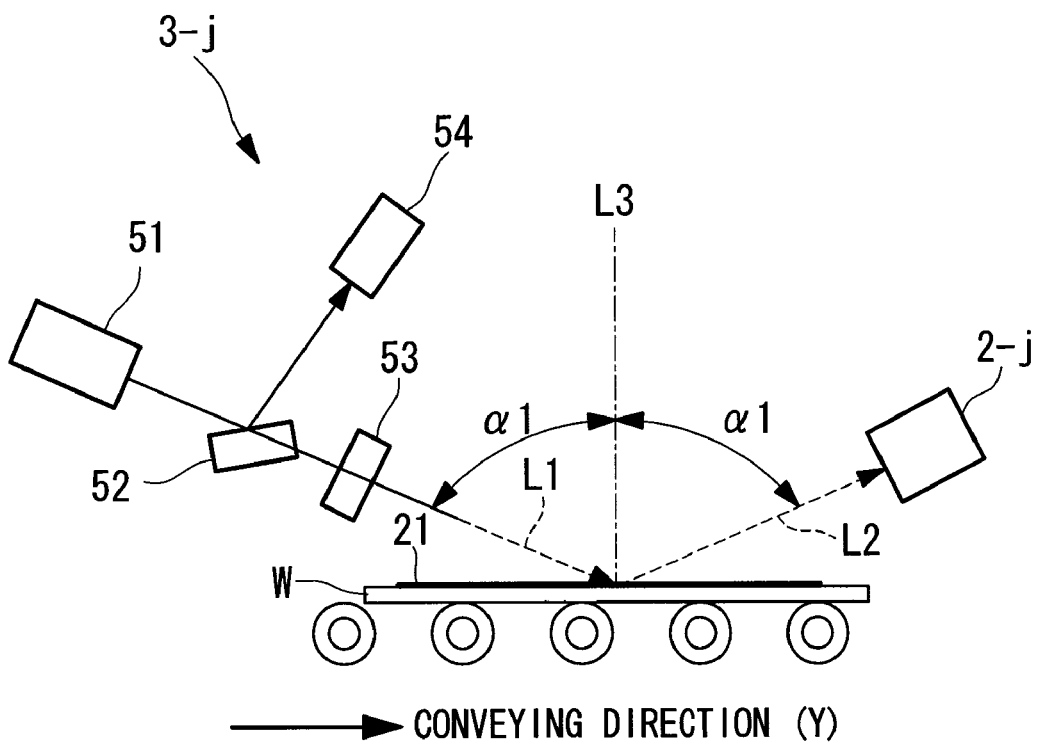
FIG. 9 is a diagram illustrating the schematic configuration of a light emitter according to the first embodiment of the present invention.
Figure 9:
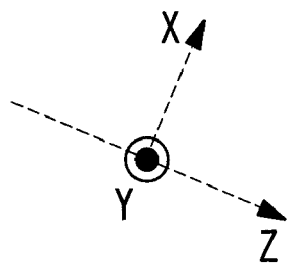

As shown in FIG. 9, each light emitter 3-j (j=1 to m) includes a light source 51 that outputs light with the wavelength selected by the test-condition selecting method performed beforehand, a half mirror (light splitter) 52 that is provided in an optical path of the emission light emitted from the light source 51 and that transmits and guides a portion of the emission light toward the substrate 11 while reflecting the remaining light, a polarizing element (polarizer) 53 that converts the light transmitted through the half mirror 52 to a p-polarization state, and a split-light detector (split-light detector) 54 that detects the light reflected by the half mirror 52.

Although a half mirror is used as means for splitting the emission light in this embodiment, the means is not limited thereto and may alternatively be, for example, a beam splitter and the like. Furthermore, the transmission-reflection ratio can be set in a freely-chosen manner.

In this embodiment, the light source 51 is, for example, a light-emitting diode (LED).

In each light emitter 3-j having such a configuration, the light source 51 emits light with a predetermined wavelength as emission light toward the transparent conductive film on the substrate 11 on the basis of a trigger signal T2 output from the information processor 7. Thus, emission light L1 with a predetermined wavelength is emitted from the light source 51 toward a measurement region on the surface of the substrate 11 conveyed on the conveyor 1. Regarding the emission light L1, a portion thereof is transmitted through the half mirror 52 so as to be guided to the transparent conductive film formed on the substrate 11, whereas the remaining portion thereof is reflected so as to be guided to the split-light detector 54. The emission light transmitted through the half mirror 52 is converted to a p-polarization state by the polarizing element 53 before being made incident on the transparent conductive film at an incidence angle α1 relative to a normal L3 to the surface of the substrate 11. This incidence angle α1 is an incidence angle selected by the test-condition selecting method performed beforehand.

The emission light L1 incident on the transparent conductive film is reflected as reflected light L2 by an angle α1 substantially equal to the incidence angle α1. The corresponding light detector 2-j optically receives the reflected light L2 reflected by the transparent conductive film. The portion of the light reflected by the half mirror 52 is optically received by the split-light detector 54.

Although each light source 51 is disposed such that the emission light is made incident at the incidence angle α1 in this embodiment, the configuration is not limited to this and an optical-path changer, such as a mirror, that changes the optical path may be provided in the optical path of the emission light emitted from the light source 51 such that the emission light is ultimately made incident on the transparent conductive film at the incidence angle α1.

FIG. 10 is a schematic diagram illustrating the positional relationship between the multiple light emitters 3-1 to 3-m and the multiple light detectors 2-1 to 2-m in the resistivity testing device 10. The multiple light emitters 3-1 to 3-m are arranged in the X direction that is substantially orthogonal to the conveying direction Y of the substrate 11. The emission light rays L1 are emitted at substantially the same time toward measurement positions M1 to Mm arranged in the X direction on the substrate 11. The multiple light detectors 2-1 to 2-m optically receive the reflected light rays L2 reflected from the measurement positions M1 to Mm at substantially the same time. Referring to a light emitter 3-j and light detector 2-j pair, the light emitter 3-j emits the emission light L1 toward a measurement position Mj. The light detector 2-j optically receives the reflected light L2 reflected from the measurement position Mj.

Figure 11:
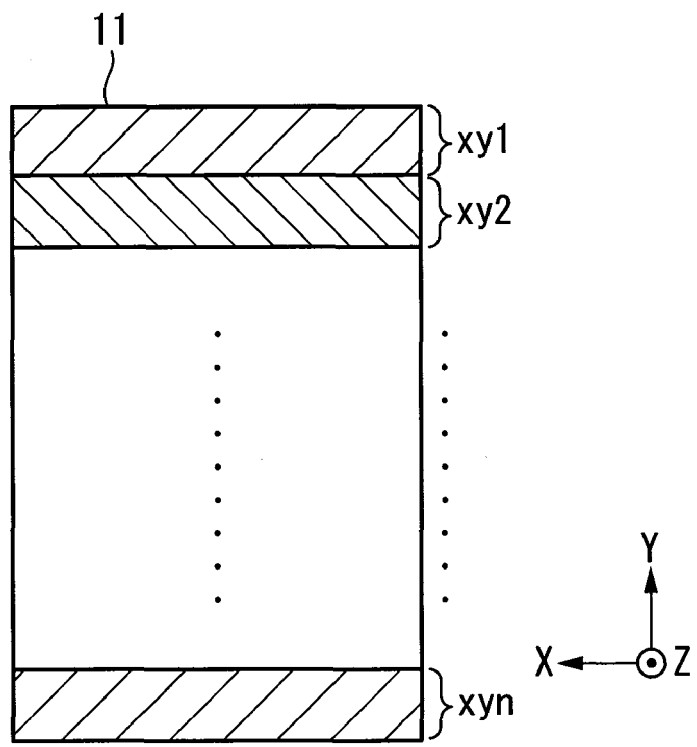
FIG. 11 is a schematic diagram illustrating measurement regions in a substrate.

FIG. 11 is a schematic diagram illustrating measurement regions in the substrate. In the substrate 11, a region to be measured in a single measurement process using the multiple light emitters 3-1 to 3-m and the multiple light detectors 2-1 to 2-m corresponds to one of measurement regions xyi (i=1, 2, ..., n) arranged in a row. The substrate 11 is moved relative to the light emitting device 3 and the light detecting device 2 by the conveyor 1. Therefore, on the basis of this movement, the light emitting device 3 and the light detecting device 2 perform measurement from a measurement region xy1 to a measurement region xyn in that order.

Upon reception of the trigger signal T2 from the information processor 7, the light emitting device 3 emits the emission light L1 to one of the measurement regions xyi of the substrate 11. Upon reception of the trigger signal T1 from the information processor 7, the light detecting device 2 optically receives the reflected light L2 reflected from the measurement region xyi of the substrate 11. Then, an intensity PSi of the received reflected light L2 is sent to the information processor 7. By repeating the series of steps including the measurement performed on the measurement region xyi and the sending of the intensity PSi of the reflected light L2 to the information processor 7 (i=1 to n), the overall characteristics of the transparent conductive film on the substrate 11 can be ultimately measured.

By sequentially performing the measurement at the measurement regions xyi of the substrate 11 conveyed on the conveyor 1 in this manner, the measurement can be performed on the entire substrate 11, which may have a large area. The light emitting device 3 may be of any type so long as it can emit the emission light L1 to one of the measurement regions xyi. Therefore, a large-scale expensive device that can emit light to the entire substrate 11 having a large area is not necessary. Consequently, the manufacturing cost can be minimized. The light detecting device 2 may be of any type so long as it can detect the reflected light L2 from one of the measurement regions xyi. Therefore, a large-scale expensive device that can optically receive light from the entire substrate 11 having a large area is not necessary. Consequently, the manufacturing cost can be minimized.

The position sensor 5 detects whether or not the substrate 11, which is a target object to be measured, is located at a predetermined position. When detected, the position sensor 5 sends a notification signal N to the information processor 7 to notify it that the substrate 11 is located at the predetermined position. The predetermined position is defined as, for example, a position corresponding to when the measurement region xy1 to be measured first reaches an emission area (i.e., an area over which the emission light is emitted) of the light emitting device 3. However, this definition is only an example and is not limited.

The rotary encoder 6 is fitted into one of center holes 1A-i (i=1, 2, ..., n) formed in the center of the respective rollers 1a-i so as to be connected to the corresponding roller 1a-i, and detects the rotation speed of the roller 1a-i. Furthermore, the rotary encoder 6 sends a (preset) pulse signal P of several pulses to several hundreds of pulses per rotation of the roller 1a-i to the information processor 7, depending on the rotation speed of the roller 1a-i.

The information processor 7 is, for example, a personal computer and includes a CPU (central processing unit), a main storage device such as a RAM (random access memory), an auxiliary storage device such as a ROM (read-only memory) and an HDD (hard disk drive), input devices such as a keyboard and a mouse, and a display device. The auxiliary storage device stores various programs, and the CPU loads a program from the auxiliary storage device into the main storage device, such as the RAM, and executes the program so as to implement various processing. For example, various processing steps for implementing a resistivity measuring method, to be described later, are stored in the auxiliary storage device in the form of a program, and the CPU loads this program into the RAM or the like and executes the program, thereby implementing evaluation-value calculation processing (evaluation-value calculator) for calculating the reflectivity, which is an evaluation value related to the amount of light of the reflected light, and reflectivity calculation processing (resistance-value calculator) for calculating the resistivity using this evaluation value.

The information processor 7 receives the notification signal N from the position sensor 5 and also receives the pulse signal P from the rotary encoder 6. Every time the pulse signal P of a single pulse is received, the trigger signal T1 and the trigger signal T2 are sent once to the light detecting device 2 and the light emitting device 3, respectively. Specifically, the information processor 7 sends the trigger signals T1 and T2 several times to several hundred times per single rotation of each roller 1a-i. The rotation speed of the roller 1a-i corresponds to the rate at which the measurement is performed at each measurement region xyi of the substrate 11. The rotation speed of the roller 1a-i corresponds to the conveying rate of the substrate 11.

The information processor 7 calculates a reflectivity Rj at each measurement position Mj (j=1 to m) in each measurement region xyi. Specifically, the information processor 7 calculates an intensity IL1j of the emission light L1 emitted to the transparent conductive film on the basis of the light intensity measured by the split-light detector 54 of each light emitter 3-j (j=1 to m) and then calculates the reflectivity Rj at the measurement position Mj using the following equation (1) on the basis of the intensity IL1j of the emission light L1 and an intensity IL2j of the reflected light L2 detected by the corresponding light detector 2-j (j=1 to m).

In this case, the intensity $IL1j$ of the emission light L1 emitted to the transparent conductive film is calculated on the basis of the reflection/transmission characteristics of the half mirror 52.

$$Rj = IL2j/IL1j \times 100 (\%) \quad (1)$$

On the basis of the calculated reflectivities R1 to Rm at the respective measurement positions M1 to Mm, the information processor 7 refers to the characteristics of the target object being measured, such as a pre-registered calibration curve in which the reflectivity and the resistivity are associated with each other, stored in a storage section (not shown) of the information processor 7 so as to determine the resistivity of the transparent conductive film at each of the measurement positions M1 to Mm in each measurement region xyi. Furthermore, this operation is performed on all of the measurement regions xy1 to xyn so as to calculate the resistivity at each measurement position in the entire transparent conductive film on the substrate 11.

In place of the aforementioned calibration curve, an arithmetic equation with the reflectivity and the resistivity as parameters may be used to calculate the resistivity.

Based on the following equation (2), the information processor 7 may further calculate the sheet resistance at each of the measurement positions M1 to Mm in each measurement region xyi by using the film thickness at the measurement position.

$$\text{Sheet Resistance } (\Omega/\text{sq}) = \text{Resistivity } (\Omega\text{cm})/\text{Film Thickness (cm)} \quad (2)$$

Accordingly, the sheet resistance (sheet resistance distribution) of the entire transparent conductive film on the substrate 11 can also be measured. With regard to the film thickness at each measurement position, information measured by another device, for example, can be used.

Next, the operation of the resistivity testing device 10 according to this embodiment will be described with reference to FIG. 12.

First, in a previous step, the transparent conductive film is formed on the substrate 11. Then, the substrate 11 with the transparent conductive film formed thereon is conveyed in the conveying direction Y on the conveyor 1 (step SB1).

The position sensor 5 detects that the substrate 11 has reached the predetermined position and sends the notification signal N to the information processor 7. In response to rotation of each roller 1a-i occurring with the conveying operation of the conveyor 1, the rotary encoder 6 sends the pulse signal P to the information processor 7. The information processor 7 receives the notification signal N from the position sensor 5 and the pulse signal P from the rotary encoder 6. After receiving the notification signal N, the information processor 7 sends the trigger signal T1 and the trigger signal T2 once to the light detecting device 2 and the light emitting device 3, respectively, every time the pulse signal P of a single pulse is received (step SB2).

Upon reception of the trigger signal T2 from the information processor 7, the light sources 51 of the multiple light emitters 3-1 to 3-m emit emission light rays. A portion of each emitted light ray is reflected by the corresponding half mirror 52, whereas the remaining portion is guided to the corresponding polarizing element 53. The emission light ray guided to the polarizing element 53 is converted to p-polarized light, which is then emitted as emission light L1 to the corresponding one of the measurement positions M1 to Mm in the measurement region xy1 of the transparent conductive film formed on the substrate 11 (step SB3).

Upon reception of the trigger signal T1 from the information processor 7, the multiple light detectors 2-1 to 2-$m$ respectively receive reflected light rays L2 reflected from the measurement positions M1 to Mm in the measurement region xy1 of the transparent conductive film. Then, the light detectors 2-1 to 2-$m$ send intensities PS1 of the received reflected light rays L2 to the information processor 7 (step SB4).

The portion of each emission light ray reflected by the half mirror 52 is guided to and optically received by the split-light detector 54 of each of the light emitters 3-1 to 3-$m$. The split-light detector 54 sends an intensity PS2 of the optically received emission light ray to the information processor 7 (step SB5). In this case, the required number of split-light detectors 54 corresponds to the number of channels.

The information processor 7 calculates the intensity $IL1j$ of the emission light L1 emitted to the transparent conductive film by using the intensity PS2 received from each split-light detector 54 (step SB6), and calculates the reflectivity $Rj$ at each of the measurement positions M1 to Mm on the basis of the intensity $IL1j$ and the intensity $IL2j$ of the reflected light L2 at the corresponding one of the light detectors 2-1 to 2-$m$ (step SB7).

Then, on the basis of the calculated reflectivities $Rj$ at the respective measurement positions M1 to Mm, the information processor 7 refers to the resistivity-reflectivity relationship (e.g., a calibration curve or an arithmetic equation in which the reflectivity and the resistivity are associated with each other) stored in the storage section so as to determine the resistivity of the transparent conductive film at the measurement positions M1 to Mm in each measurement region xyi. Moreover, the sheet resistance may be calculated by using film-thickness information measured by another device. The information processor 7 stores the calculation results in the storage section.

Subsequently, the information processor 7 determines whether or not the resistivity calculation is completed for all of the measurement regions xy1 to xyn (step SB8). For example, this can be determined when the number of pulse signals P received from the rotary encoder 6 after receiving the notification signal N from the position sensor 5 reaches a value n. Thus, the characteristics of the entire transparent conductive film on the substrate 11 can be measured. If not completed, the operation returns to step SB2 so as to perform the above-described process.

On the other hand, when completed, the information processor 7 determines whether or not the transparent conductive film has desired characteristics on the basis of the characteristics of the entire transparent conductive film on the substrate 11 stored in the storage section (step SB9). A conceivable determination method includes, for example, the following method.

For example, a reference resistivity value of the transparent conductive film preliminarily stored in the storage section is compared with the resistivities at the measurement positions M1 to Mm in each of the measurement regions xy1 to xyn, and if the number of measurement positions not satisfying the reference value is greater than or equal to a predetermined numerical value (stored in the storage section), it is determined that the transparent conductive film is defective. Alternatively, the determination can be performed by statistically processing the distribution of the deviation between the reference value and each measurement result. As a further alternative, the transparent conductive film may be determined as being defective if at least one of the resistivity and the sheet resistance (and film thickness) does not satisfy the reference value. The present invention is not limited to these determination methods.

If defective, the substrate 11 with the transparent conductive film formed thereon is removed from the manufacturing process (step SB10).

By repeatedly performing the above-described operation, the testing of the resistivity of the transparent conductive film is repeatedly performed.

As described above, with the resistivity testing method and the resistivity testing device according to this embodiment, since an optical technique is used for measuring the resistivity of the transparent conductive film, the resistivity can be calculated in a short time in a non-contact manner. Furthermore, by using reflectivity, an adverse effect of the substrate, such as glass, can be reduced, as compared with using transmissivity. Moreover, since the emission light is converted to p-polarized light and the resistivity is calculated using the Brewster effect, various measurement errors, such as an error in film thickness, can be eliminated, whereby the resistivity can be calculated with high accuracy.

Although m light emitters and m light detectors are provided in the above-described embodiment, the m light emitters and the m light detectors may be integrated into a single detecting unit, and multiple (e.g., eight) detecting units may be arranged parallel to each other with a predetermined distance therebetween in the conveying direction (Y direction) of the substrate.

Thus, the emission light can be emitted to a wide area of the film surface of the transparent conductive film, and the reflected light thereof can be detected. This allows for efficient testing of the resistivity.

Second Embodiment

Next, a resistivity testing device and a method therefor according to a second embodiment of the present invention will be described with reference to the drawings.

In the resistivity testing device according to this embodiment, the configuration of each of light emitters 3a-j (j=1 to m) of a light emitting device differs from the configuration of each of the light emitters 3-j (j=1 to m) of the light emitting device 3 in the first embodiment. The following description of the resistivity testing device according to this embodiment omits the descriptions of the features that are the same as those in the first embodiment and mainly includes descriptions of features that differ therefrom.

Figure 13:
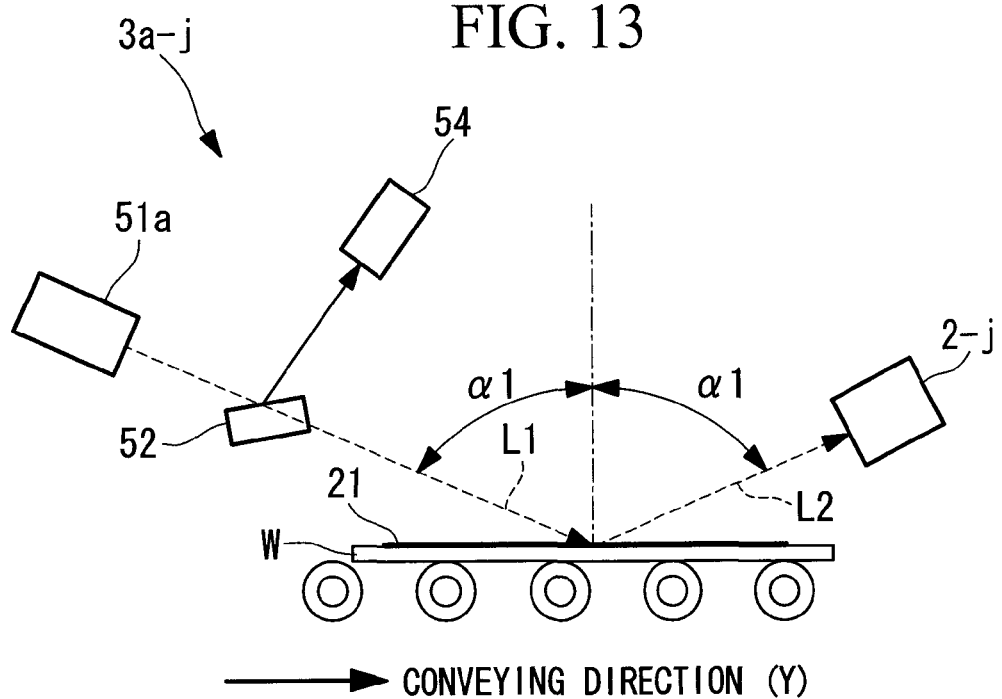
FIG. 13 is a diagram illustrating the schematic configuration of a light emitter used in a resistivity testing device according to a second embodiment of the present invention.

FIG. 13 is a schematic diagram illustrating the configuration of the light emitting device in the resistivity testing device according to the present invention. In each of the light emitters 3a-j (j=1 to m) according to this embodiment, a semiconductor laser is used as a light source 51a. Thus, the polarizing element 53 (see FIG. 9) that converts emission light L1 to a p-polarization state is not necessary. Furthermore, since semiconductor lasers have higher directivity than other types of light sources, such as the light-emitting diodes mentioned above, the light emitters 3a can be disposed distant from the transparent conductive film, which is a target test object. This is effective, for example, when the target test object is hot or when dust particles or the like scatter from the target test object.

Furthermore, since semiconductor lasers are used, the light sources 51 can be combined with optical fibers, whereby the configuration of a header section of the light emitting device 3 fixed to the resistivity testing device can be made compact.

Third Embodiment

Next, a resistivity testing device and a method therefor according to a third embodiment of the present invention will be described with reference to the drawings.

In the resistivity testing device according to this embodiment, the configuration of light emitters 3b-j (j=1 to m) differs from that of the light emitters 3-j (j=1 to m) in the first embodiment. The following description of the resistivity testing device according to this embodiment omits the descriptions of the features that are the same as those in the first embodiment and mainly includes descriptions of features that differ therefrom.

Figure 14:
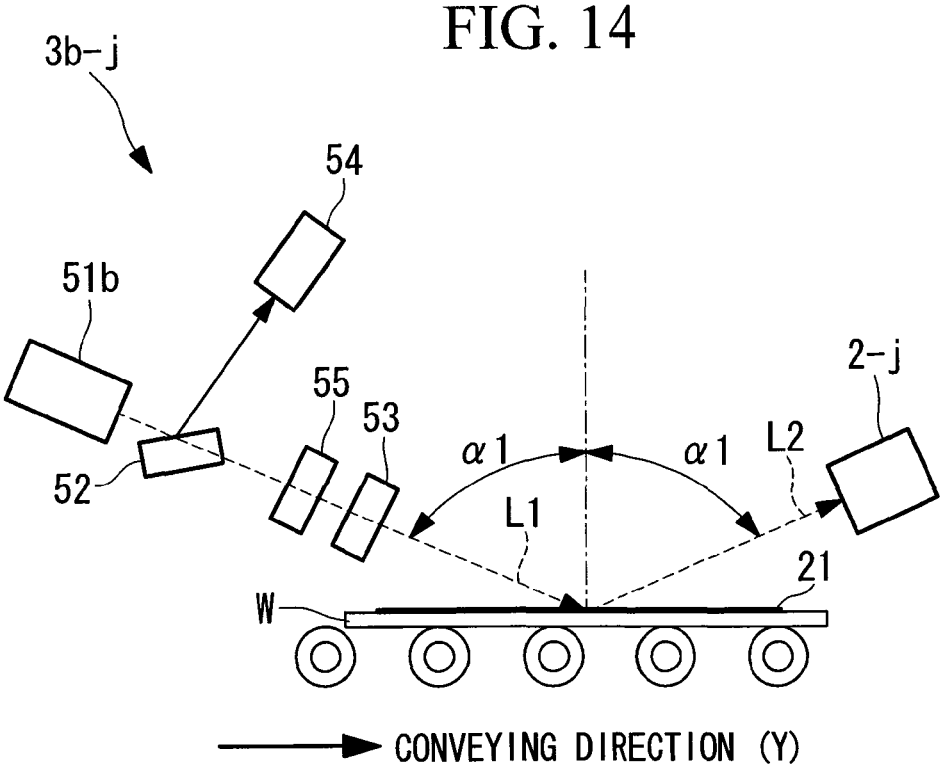
FIG. 14 is a diagram illustrating the schematic configuration of a light emitter used in a resistivity testing device according to a third embodiment of the present invention.

FIG. 14 is a schematic diagram illustrating the configuration of one of the light emitters 3b-j (j=1 to m) in the resistivity testing device according to the present invention. In each of the light emitters 3b-j (j=1 to m) according to this embodiment, a light source that emits light in a wide band is used as a light source 51b. The light source 51b used here is configured to emit emission light that at least includes light in a wavelength range selected by the above-described test-condition selecting method. A tungsten lamp or the like may be used as the light source 51b.

Furthermore, in each of the light emitters 3b-j (j=1 to m) according to this embodiment, a wavelength selecting element (wavelength selector) 55, such as a band-pass filter or an interference filter, that selects a specific wavelength from emission light in a wide wavelength band, that is, emission light in the wavelength range selected by the above-described test-condition selecting method, is provided in an optical path of emission light L1 or in an optical path of reflected light L2. FIG. 14 illustrates an example where the wavelength selecting element 55 is provided in the optical path of the emission light L1.

The bandwidth of the wavelength selecting element 55 preferably ranges between several tens of nanometers and several hundreds of nanometers. In detail, it is preferable that an appropriate bandwidth be set experimentally while taking into account a reduced SN-ratio caused by a reduction in the amount of light and a resistivity measurement error caused by the wider bandwidth.

Fourth Embodiment

Next, a resistivity testing device and a method therefor according to a fourth embodiment of the present invention will be described with reference to the drawings.

In the resistivity testing device according to each of the above-described embodiments, the half mirrors 52 that reflect a portion of the emission light L1 are provided in the optical path of the emission light L1, and the split-light detectors 54 that detect the portion of the emission light split by the half mirrors 52 are provided (for example, see FIG. 9).

Figure 15:
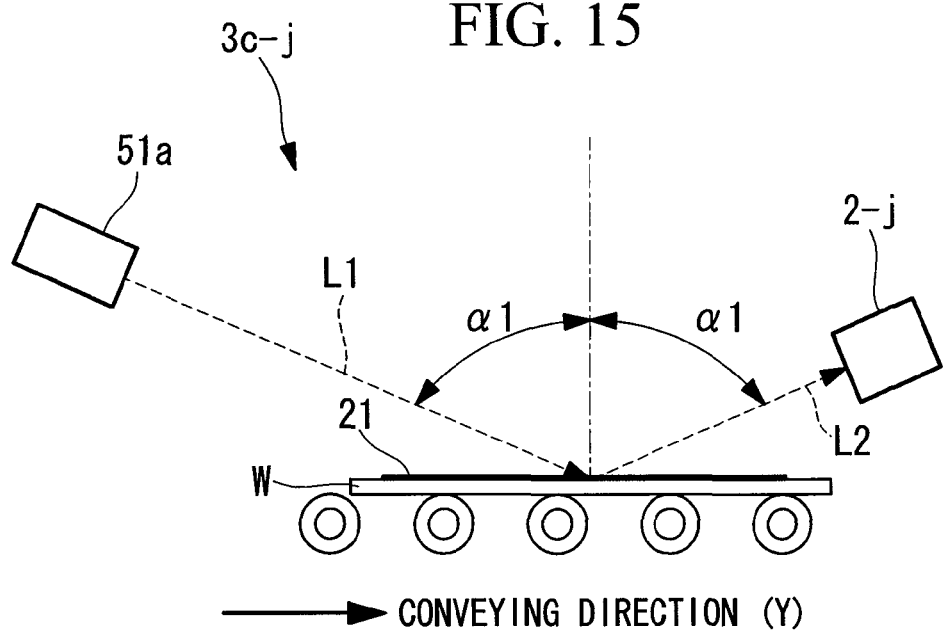
FIG. 15 is a schematic diagram illustrating the schematic configuration of a light emitter used in a resistivity testing device according to a fourth embodiment of the present invention.

In this embodiment, the half mirrors 52 and the split-light detectors 54 are omitted. FIG. 15 illustrates an example of a schematic configuration of one of light emitters 3c-j according to this embodiment, equipped with a semiconductor laser as the light source 51a, like each of the light emitters 3a-j according to the second embodiment described above.

Figure 12:
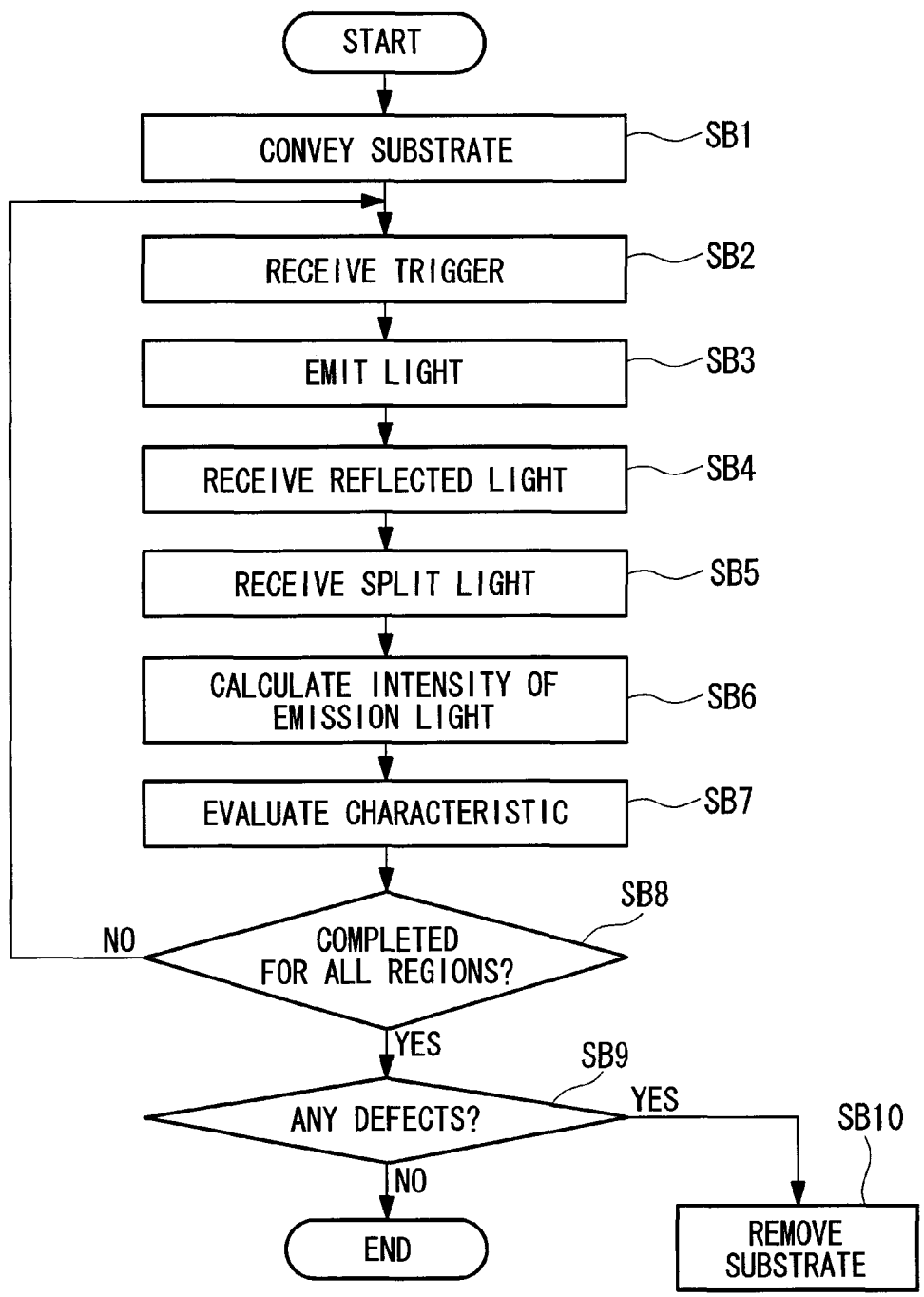
FIG. 12 is a flow chart illustrating the procedure of a resistivity testing method according to the first embodiment of the present invention.

With the configuration in which the half mirrors 52 and the split-light detectors 54 are omitted in this manner, since the intensity of the emission light L1 cannot be sequentially calculated, as in the above-described embodiments, steps SB5 and SB6 shown in FIG. 12 are omitted; it can thus be conceived that the resistivity calculation accuracy may be somewhat lowered, as compared with when the light emitters 3-j according to the first embodiment shown in FIG. 9 are used. However, since the aforementioned components can be omitted, as shown in FIG. 15, the device configuration can be simplified and made compact.

Fifth Embodiment

Next, a resistivity testing device and a method therefor according to a fifth embodiment of the present invention will be described.

The resistivity testing device according to this embodiment differs from the resistivity testing device according to the first embodiment in that the light detecting device 2 and the light emitting device 3 according to each of the above-described embodiments are surrounded by a shielding member.

By surrounding the light detecting device 2 and the light emitting device 3 with a shielding member in this manner, entry of ambient light can be suppressed, thereby increasing the resistivity measurement accuracy.

{Photoelectric Converter}

Next, a photoelectric converter according to an embodiment of the present invention, manufactured by using the resistivity testing device according to any one of the above-described embodiments, will be described.

Figure 16:
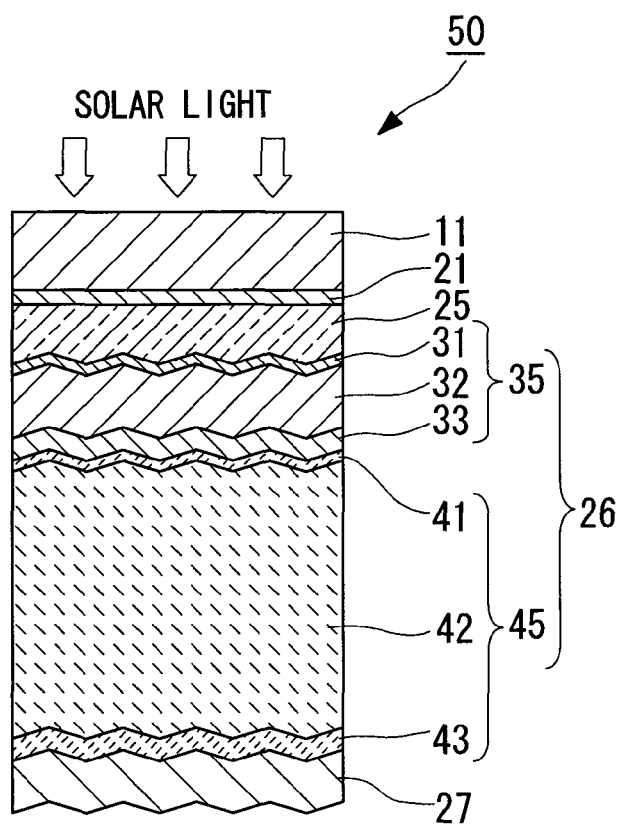
FIG. 16 is a cross-sectional view illustrating an example of a photoelectric converter manufactured by using the resistivity testing device according to any one of the embodiments of the present invention.

FIG. 16 is a cross-sectional view illustrating an example of a photoelectric converter manufactured by using the resistivity testing device according to any one of the above-described embodiments of the present invention. A tandem solar cell 50 will be described as an example of a photoelectric converter. A transparent conductive film to be tested by the resistivity testing device according to the present invention is not limited to this example and may be used in other types of solar cells (e.g., an amorphous solar cell or a crystalline solar cell).

The tandem solar cell 50 includes a substrate 11, an alkaline barrier film 21, a transparent conductive film 25, a battery layer 26, and an underside electrode film 27. The battery layer 26 includes an amorphous silicon-based battery layer 35 and a microcrystalline silicon-based battery layer 45. The amorphous silicon-based battery layer 35 includes an amorphous p-layer film 31, an amorphous i-layer film 32, and a microcrystalline n-layer film 33. A buffer layer for enhancing interfacial characteristics may be provided between the amorphous p-layer film 31 and the amorphous i-layer film 32. The microcrystalline silicon-based battery layer 45 includes a microcrystalline p-layer film 41, a microcrystalline i-layer film 42, and a microcrystalline p-layer film 43. An intermediate layer, such as GZO (Ga-doped ZnO film), which is to become a semi-reflective film for enhancing light absorption of the amorphous layer 35, may be provided between the microcrystalline n-layer film 33 and the microcrystalline p-layer film 41 by being formed to a film thickness of 20 nm to 100 nm by using a sputtering device.

{Manufacturing Apparatus and Manufacturing Method for Photoelectric Converter}

Next, a solar-cell manufacturing apparatus and a method therefor to which the resistivity testing device of the present invention is applied will be described. An example of an apparatus and a method for manufacturing the tandem solar cell 50 shown in FIG. 16 will be described here.

Figure 17:
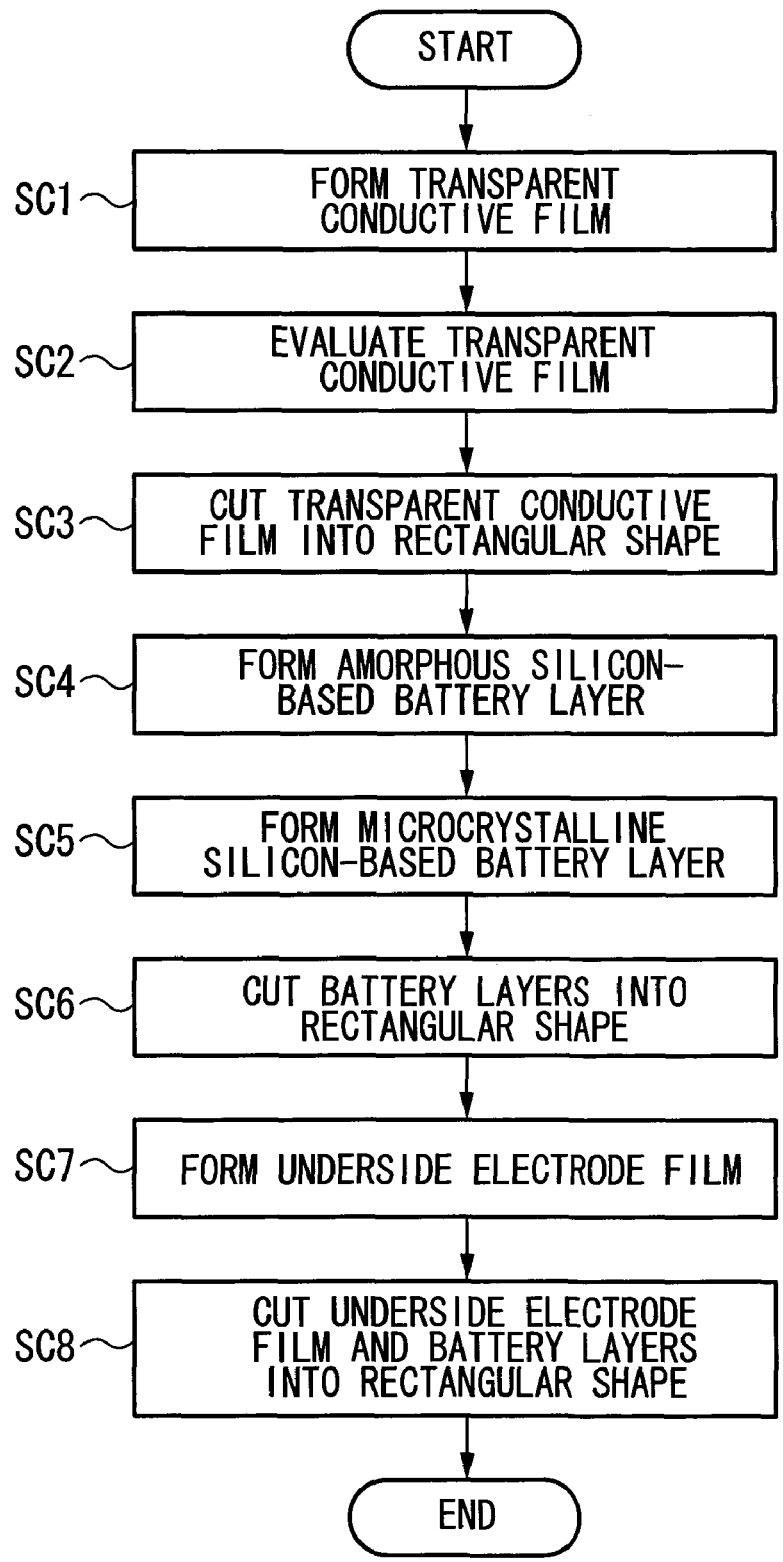
FIG. 17 is a flow chart illustrating the procedure of a solar-cell manufacturing method according to an embodiment of the present invention.
Figure 18:
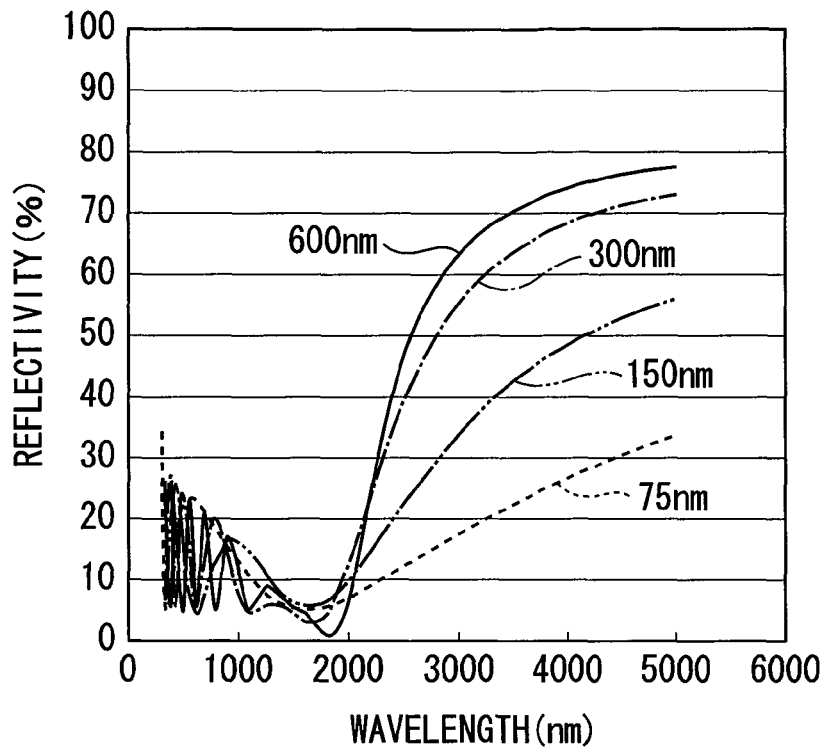
FIG. 18 is a diagram illustrating a reflectivity-versus-wavelength relationship for each film thickness.
Figure 19:
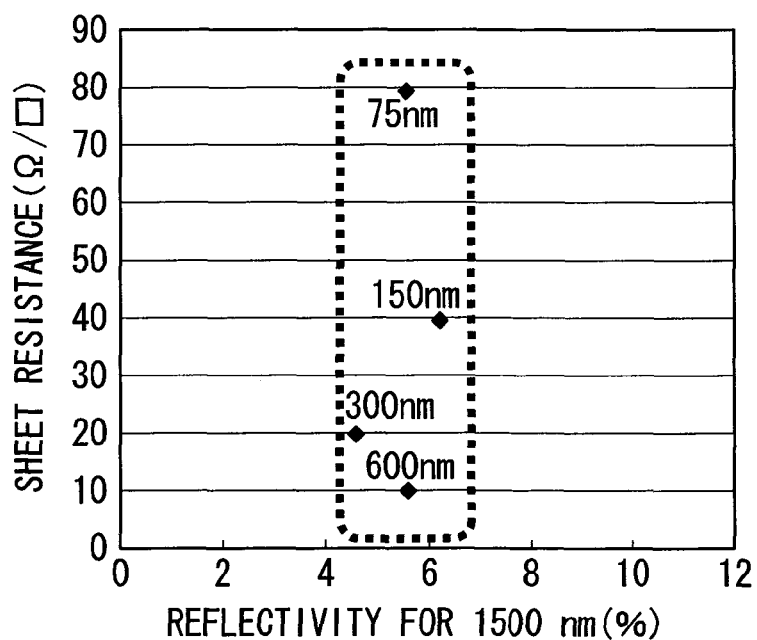
FIG. 19 is a diagram illustrating a sheet-resistance-versus-reflectivity relationship for each film thickness when a wavelength of 1500 nm is used.
Figure 20:
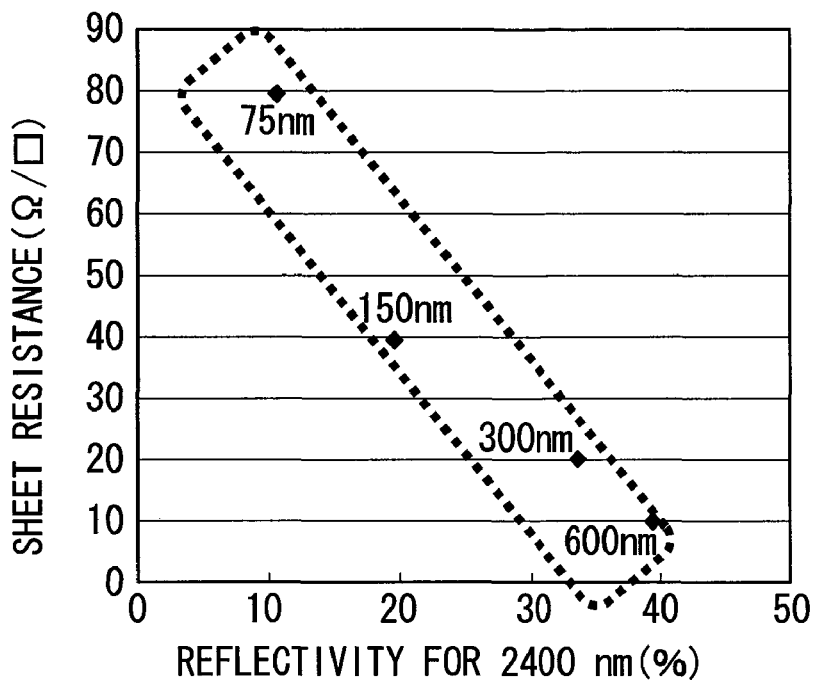
FIG. 20 is a diagram illustrating a sheet-resistance-versus-reflectivity relationship for each film thickness when a wavelength of 2400 nm is used.
Figure 21:
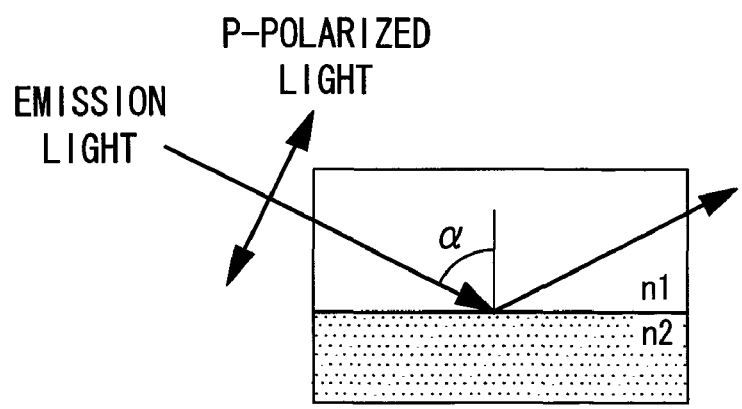
FIG. 21 is a diagram illustrating an optical calculation model of the Brewster effect.
Figure 22:
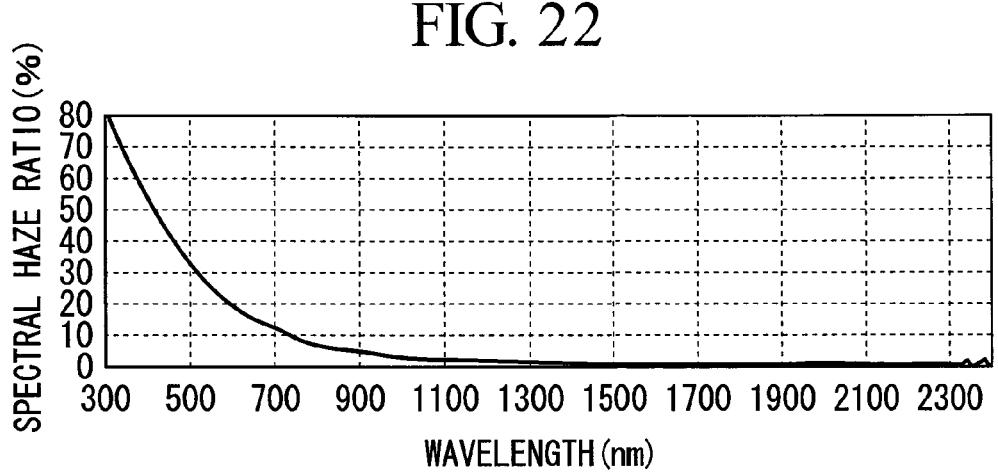
FIG. 22 is a diagram illustrating the relationship between a spectral haze ratio and each wavelength.

FIG. 17 is a flow chart illustrating the procedure of a solar-cell manufacturing method according to an embodiment of the present invention. In this embodiment, a soda float glass substrate (1.4 m×1.1 m×film thickness: 4 mm) is used as a substrate 11. It is desirable that the end surfaces of the substrate 11 be given corner-chamfering and round-chamfering treatments to prevent breakage.

First, a silicone oxide film ($SiO_2$ film) serving as an alkaline barrier film 21 is formed on the substrate 11 by thermal CVD. The substrate temperature is 500° C. and the film thickness is 20 nm to 50 nm. Next, an F-doped tin oxide film ($SnO_2$ film) serving as a transparent conductive film 25 is formed on the alkaline barrier film 21 by thermal CVD. The substrate temperature is 500° C. and the film thickness is 300 nm to 900 nm (step SC1).

Subsequently, the substrate 11 is gradually cooled while being conveyed on a conveying path, and is cooled to a range between the ambient temperature and 100° C. by a cooling device, such as a fan, provided in front of the resistivity testing device before being conveyed to the resistivity testing device according to any one of the above-described embodiments of the present invention. In the resistivity testing device, the resistivity of the transparent conductive film 25 formed on the substrate 11 is tested (step SC2), and if the transparent conductive film 25 on the substrate 11 does not satisfy a desired criterion, the substrate 11 is removed from the manufacturing process.

Accordingly, even when a defect occurs in the transparent conductive film 25 in the film forming process thereof, such a defect can be ascertained at an early stage so that production of substrates 11 having formed thereon transparent conductive films 25 not satisfying desired characteristics can be minimized. When using large-size substrates 11, since the costs required for the substrates 11 and for the film formation are extremely high, the wasting of such costs can be prevented. In addition, a malfunction in transparent-conductive-film manufacturing equipment can also be detected. Consequently, inspection of the manufacturing equipment or adjustment of film-forming conditions can be immediately carried out, thereby maintaining productivity.

Subsequently, the substrate 11 is set on an X-Y table. Then, by irradiating a predetermined position on the substrate 11 with the first harmonic (1064 nm) of a laser-diode-pumped YAG laser, the transparent conductive film and the alkaline barrier film are processed so as to be given a predetermined rectangular shape (step SC3).

Subsequently, by using a plasma CVD device, an amorphous p-layer film 31 and an amorphous i-layer film 32 serving as an amorphous silicon-based battery layer 35 are sequentially formed under a reduced-pressure atmosphere of 30 Pa to 150 Pa at a temperature of about 200° C. Then, a microcrystalline p-layer film 33 is formed under a reduced-pressure atmosphere of 30 Pa to 150 Pa at a substrate temperature of 180° C. (step SC4). The amorphous p-layer film 31 is mainly composed of B-doped amorphous SiC and has a film thickness of 10 nm to 30 nm. The amorphous i-layer film 32 is mainly composed of amorphous Si and has a film thickness of 200 nm to 350 nm. The microcrystalline n-layer film 33 is mainly composed of P-doped microcrystalline Si and has a film thickness of 30 nm to 50 nm.

Subsequently, by using the plasma CVD device, a microcrystalline p-layer film 41 of a microcrystalline silicon battery layer 45 is formed under a reduced-pressure atmosphere of 30 Pa to 700 Pa at a substrate temperature of 150° C. to 250° C. Then, a microcrystalline i-layer film 42 is formed under a reduced-pressure atmosphere of 900 Pa to 3000 Pa at a substrate temperature of 150° C. to 250° C. Subsequently, a microcrystalline n-layer film 43 is formed under a reduced-pressure atmosphere of 30 Pa to 700 Pa at a substrate temperature of 150° C. to 250° C. (step SC5). The microcrystalline p-layer film 41 is mainly composed of B-doped microcrystalline Si and has a film thickness of 10 nm to 50 nm. The microcrystalline i-layer film 42 is mainly composed of microcrystalline Si and has a film thickness of 1.5 μm to 3 μm. The microcrystalline n-layer film 43 is mainly composed of P-doped microcrystalline Si and has a film thickness of 20 nm to 50 nm.

Subsequently, the substrate 11 is set on the X-Y table. Then, by irradiating a predetermined position on the substrate 11 with the second harmonic (532 nm) of the laser-diode-pumped YAG laser, the battery layer 26 is processed so as to be given a predetermined rectangular shape (step SC6).

By using the sputtering device, a Ag film and a Ti film as an underside electrode film 27 are sequentially formed under a reduced-pressure atmosphere of 1 Pa to 5 Pa at a temperature of about 150° C. (step SC7). Regarding the underside electrode film 27 in this embodiment, the Ag film of 200 nm to 500 nm and the Ti film of 10 nm to 20 nm are stacked in that order.

Subsequently, the substrate 11 is set on the X-Y table. Then, by irradiating a predetermined position on the substrate 11 with the second harmonic (532 nm) of the laser-diode-pumped YAG laser, the underside electrode film 27 is processed so as to be given a predetermined rectangular shape (step SC8).

With the above-described steps, a photoelectric converter can be manufactured.

As described above, with the photoelectric-converter manufacturing method according to this embodiment, since the resistivity testing device and the method therefor according to any one of the embodiments of the present invention are used, a defect occurring in the transparent conductive film in the film forming process thereof can be ascertained before completion of a solar cell. Consequently, production of a solar cell that does not satisfy the desired characteristics due to a defect in the transparent conductive film can be prevented at an early stage. Furthermore, the electrical characteristics of the transparent conductive film can be tested in a short time in a non-contact manner in the course of the manufacturing process of the solar cell. In addition, a malfunction in the transparent-conductive-film manufacturing equipment can also be detected. Consequently, inspection of the manufacturing equipment or adjustment of film-forming conditions can be immediately carried out, thereby maintaining productivity.

Figure 23:
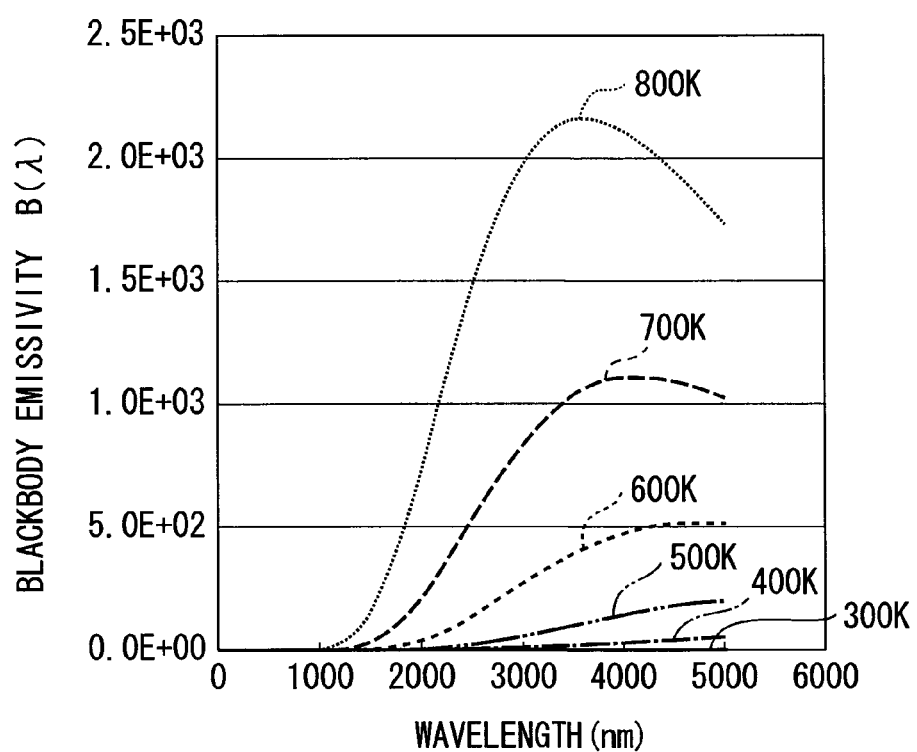
FIG. 23 is a diagram illustrating a blackbody-emissivity-versus-wavelength relationship at each temperature.

Although the resistivity testing device is provided on the downstream side of the cooling device in the above-described embodiment, the invention is not limited to such an arrangement example. For example, the resistivity testing device can alternatively be provided on the upstream side of the cooling device. In that case, since the temperature of the substrate is not stable, that is, the substrate temperature deviates from the assumed range between the ambient temperature and 100° C. in the present invention, there is a possibility that a measurement error may occur depending on the temperature, as shown in FIG. 23. Therefore, if a substrate with unstable temperature is to be tested, calibration curves in which the reflectivity and the resistivity are associated with each other in accordance with the substrate temperature are prepared, so that when performing the testing, the temperature of the substrate is measured and the resistivity is obtained from the reflectivity by using the calibration curve that corresponds to that temperature.

REFERENCE SIGNS LIST 1 conveyor
1a-i (i=1, 2, . . . , n) roller
1A-i (i=1, 2, . . . , n) center hole
2 light detecting device
2-1 to 2-m, 2-j light detector
3 light emitting device
3-1 to 3-m, 3-j, 3a-j, 3b-j, 3c-j light emitter
5 position sensor
6 rotary encoder
7 information processor
8 (8a, 8b) detector securing member
9 (9a, 9b) light-source securing member
10 resistivity testing device
11 substrate
25 transparent conductive film
50 solar cell
51, 51a, 51b light source
52 half mirror
53 polarizing element
54 split-light detector

The invention claimed is:

1. A test-condition selecting method for selecting a wavelength and an incidence angle of emission light used for testing the resistivity of a transparent conductive film, comprising:
emitting p-polarized emission light rays having different test conditions, including wavelengths and incidence angles, to a plurality of transparent conductive films having different combinations of film thicknesses and resistivities so as to measure evaluation values related to amounts of light of reflected light rays thereof;
obtaining a correlation in which the test conditions, the evaluation values, and sample conditions are associated with each other, the sample conditions including combinations of the film thicknesses and the resistivities of the transparent conductive films; and
selecting one of the test conditions in the correlation, the test condition being such that an error in the corresponding evaluation value due to the different film thicknesses of the transparent conductive films is within a tolerable range and a change in the evaluation value relative to a change in the corresponding resistivity is greater than or equal to a predetermined value.

2. A resistivity testing method comprising:
emitting p-polarized emission light having a wavelength selected by the test-condition selecting method according to claim 1 toward a transparent conductive film, formed on a light-transmissive substrate conveyed along a manufacturing line, from a film-surface side at an incidence angle selected by the test-condition selecting method;
detecting reflected light reflected at the transparent conductive film;
calculating an evaluation value related to the amount of light of the reflected light with respect to the wavelength selected by the test-condition selecting method on the basis of the intensity of the detected reflected light; and
obtaining a resistivity from the calculated evaluation value by using a correlation characteristic in which the evaluation value and the resistivity are associated with each other in advance.

3. A resistivity testing device comprising:
a light emitter that emits p-polarized emission light having a wavelength selected by the test-condition selecting method according to claim 1 toward a transparent conductive film, formed on a light-transmissive substrate conveyed along a manufacturing line, from a film-surface side at an incidence angle selected by the test-condition selecting method;
a light detector that detects reflected light reflected at the transparent conductive film;
an evaluation-value calculator that calculates an evaluation value related to the amount of light of the reflected light with respect to the wavelength selected by the test-condition selecting method on the basis of the intensity of the detected reflected light; and
a resistance-value calculator that obtains a resistivity from the calculated evaluation value by using a correlation characteristic in which the evaluation value and the resistivity are associated with each other in advance.

4. The resistivity testing device according to claim 3, wherein the light emitter includes:
   a light source that emits the emission light having the wavelength, and
   a polarizer that converts the emission light emitted from the light source to the p-polarized emission light.

5. The resistivity testing device according to claim 4, wherein the light source is a light-emitting diode.

6. The resistivity testing device according to claim 3, wherein the light emitter includes:
   a light source that emits the emission light in a predetermined wavelength range that includes the wavelength;
   a polarizer that converts the emission light emitted from the light source to the p-polarized emission light; and
   a wavelength selector provided in an optical path of the emission light emitted from the light source or in an optical path of the reflected light reflected at the transparent conductive film and configured to transmit light having the wavelength selected by the test-condition selecting method and to block other wavelengths.

7. The resistivity testing device according to claim 3, wherein the light emitter includes a semiconductor laser that emits the emission light having the wavelength as a light source.

8. The resistivity testing device according to claim 3, further comprising:
   a light splitter provided in an optical path of emission light emitted from the light emitter and configured to split off a portion of the emission light; and
   a split-light detector that detects the light split off by the light splitter,
   wherein the evaluation-value calculator calculates the evaluation value by using a detection result of the split-light detector.

9. The resistivity testing device according to claim 3, wherein at least one of the light emitter and the light detector is surrounded by a light shielding member.

10. A photoelectric-converter manufacturing apparatus comprising the resistivity testing device according to claim 3 provided in a conveyor line.

11. The photoelectric-converter manufacturing apparatus according to claim 10, further comprising:
   a cooling device that cools a light-transmissive substrate on which the transparent conductive film is formed,
   wherein the resistivity testing device is provided on a downstream side of the cooling device.

12. A photoelectric converter manufactured by the photoelectric-converter manufacturing apparatus according to claim 10.

* * * * *